US011896842B2

United States Patent
Castel

(10) Patent No.: US 11,896,842 B2
(45) Date of Patent: *Feb. 13, 2024

(54) METHOD AND SYSTEM FOR IRRADIATING TISSUE WITH PULSED BLUE AND RED LIGHT TO REDUCE MUSCLE FATIGUE, ENHANCE WOUND HEALING AND TISSUE REPAIR, AND REDUCE PAIN

(71) Applicant: CAREWEAR CORP., Reno, NV (US)

(72) Inventor: John C. Castel, Reno, NV (US)

(73) Assignee: CAREWEAR CORP., Reno, NV (US)

( * ) Notice: Subject to any disclaimer, the term of this patent is extended or adjusted under 35 U.S.C. 154(b) by 285 days.

This patent is subject to a terminal disclaimer.

(21) Appl. No.: 17/242,471

(22) Filed: Apr. 28, 2021

(65) Prior Publication Data

US 2021/0244962 A1    Aug. 12, 2021

Related U.S. Application Data

(63) Continuation of application No. 16/204,310, filed on Nov. 29, 2018, now Pat. No. 11,020,605.

(60) Provisional application No. 62/677,395, filed on May 29, 2018.

(51) Int. Cl.
*A61N 5/06* (2006.01)

(52) U.S. Cl.
CPC .... *A61N 5/0613* (2013.01); *A61N 2005/0645* (2013.01); *A61N 2005/0663* (2013.01); *A61N 2005/0664* (2013.01)

(58) Field of Classification Search
CPC .......... A61N 5/0613; A61N 2005/0645; A61N 2005/0663; A61N 2005/0664; A61N 2005/0651; A61N 5/0622; A61N 5/0616
See application file for complete search history.

(56) References Cited

U.S. PATENT DOCUMENTS

| | | | |
|---|---|---|---|
| 11,020,605 B2 * | 6/2021 | Castel | A61N 5/0622 |
| 2017/0128736 A1 * | 5/2017 | Johnson | A61N 2/002 |

* cited by examiner

*Primary Examiner* — Gary Jackson
*Assistant Examiner* — Sebastian X Lukjan
(74) *Attorney, Agent, or Firm* — STINSON LLP

(57) ABSTRACT

Methods are disclosed for reduction of muscle fatigue, enhancement of wound healing and tissue repair and/or reduction of pain. The methods comprise irradiating a muscle or an injured tissue of a subject, as applicable, with pulsed blue and/or red light having an average irradiance that ranges from 0.1 mW/cm$^2$ to 20 mW/cm$^2$ at a radiant exposure that ranges from 0.5 J/cm$^2$ to 60 J/cm$^2$. The pulsed blue and/or red light is preferably applied with a flexible light source that includes a flexible light emitter positioned between a flexible anode and a flexible cathode. The flexible light emitter may comprise a printed LED film or OLEDs that emit blue and/or red light, or a printed LED film or OLEDs that emit blue light in combination with a quantum dot film that converts a portion of the blue light emission into red light.

42 Claims, 17 Drawing Sheets

METHOD AND SYSTEM FOR IRRADIATING TISSUE WITH PULSED BLUE AND RED LIGHT TO REDUCE MUSCLE FATIGUE, ENHANCE WOUND HEALING AND TISSUE REPAIR, AND REDUCE PAIN

CROSS-REFERENCE TO RELATED APPLICATIONS

This application is a continuation of and claims priority to U.S. patent application Ser. No. 16/204,310, filed on Nov. 29, 2018, which is based on and claims priority to U.S. Provisional Application Ser. No. 62/677,395, filed on May 29, 2018, each of which is incorporated herein by reference in its entirety.

STATEMENT REGARDING FEDERALLY SPONSORED RESEARCH OR DEVELOPMENT

Not applicable.

BACKGROUND OF THE INVENTION

Photobiomodulation involves the use of non-ionized light sources, including lasers and light emitting diodes (LEDs), to stimulate endogenous chromophores eliciting various biological events within the tissues. The biological events are largely dependent on the wavelength of the photobiomodulation therapy. Different wavelengths in the visible and infrared spectrums have been used to treat musculoskeletal conditions in physical medicine and rehabilitation. While photobiomodulation therapy has generally produced positive outcomes for different conditions, there is a need for improved therapies directed to the treatment of muscle fatigue and/or the healing of injured tissues.

BRIEF SUMMARY OF THE INVENTION

The present invention is directed to a method and system for irradiating tissue of a subject with pulsed blue and red light (or only pulsed blue light) in order to reduce muscle fatigue, enhance wound healing and tissue repair, and reduce pain. The pulsed blue and/or red light is preferably applied using a flexible light source in the form of a patch, pad, mask, wrap, fiber, or bandage, which contacts and conforms to the skin or tissue surface of the subject. Preferably, the light source produces the pulsed blue and/or red light with an intensity that is substantially constant across the surface of the device so as to provide a substantially uniform light emission.

In one aspect of the invention, the light source is used to reduce muscle fatigue in a subject. In use, the light source is generally placed on the skin of a subject directly over the belly of the muscle to be treated and the muscle innervation, i.e., the motor point. The underlying tissue is then irradiated with pulsed blue and red light at specified pulse parameters, dosages and time intervals. The light treatment may be used, for example, to reduce muscle fatigue caused by strenuous activity or exercise and, in some embodiments, may be particularly beneficial to athletes when applied during a sporting event.

In another aspect of the invention, the light source is used to enhance wound healing and tissue repair and reduce pain associated with various types of tissue injuries, such as muscle contusions, stretched or torn muscles, ligaments or tendons, and open skin wounds. In use, the light source is generally placed on the skin directly over the injured tissue. The underlying tissue is then irradiated with pulsed blue and red light at specified pulse parameters, dosages and time intervals. The light treatment may be used to enhance healing of the injured tissue and also provide a decrease in pain caused by the injured tissue.

In yet another aspect of the invention, the light source is used to reduce muscle fatigue, enhance wound healing and tissue repair, and reduce pain, as described above, by irradiating the tissue with pulsed blue light at specified pulse parameters, dosages and time intervals. In this case, the pulsed red light is not used.

In some embodiments, the light source used to implement the present invention has a thin layered structure that includes a flexible light emitter. In one embodiment, the flexible light emitter comprises a printed LED film laminated to a quantum dot film. The printed LED film comprises blue light emitting diodes printed on a flexible film, and the quantum dot film is used to convert a portion of the blue light emission into red light. In another embodiment, the flexible light emitter comprises both blue and red light emitting diodes printed in a checkerboard or grid-like pattern on a flexible film. In other embodiments, the printed LEDs are replaced with organic light emitting diodes (OLEDs). In yet other embodiments, the flexible light emitter comprises only blue printed LEDs or only blue OLEDs. Of course, other types of light sources may also be used in accordance with the present invention.

The light source of some embodiments also includes a flexible substrate that supports the flexible light emitter (described above) and other layers of the light source. One or more encapsulation or barrier layers may optionally be included to isolate the flexible light emitter from an ambient environment. In addition, a layer of hydrogel or a transparent adhesive film such as a silicone film or pressure sensitive adhesive (PSA) is preferably used as an adhesive to adhere the light source to the skin or tissue surface of the subject to thereby provide optical light piping and maximize optical coupling.

An electronic circuit is programmed to control the light source so that the blue and red light (or only blue light) is provided in a pulsed mode of irradiation at desired levels of irradiance (power density) and radiant exposure (fluence). In general, the pulses have a pulse duration that ranges from about 5 microseconds to about 1,000 microseconds, and the off time between pulses ranges from about 10 microseconds to about 1 second. A particularly suitable pulse repetition rate ranges from about 33 kHz to about 40 kHz. Preferably, the pulsed blue and/or red light has an average irradiance that ranges from 0.1 mW/cm$^2$ to 20 mW/cm$^2$ and is provided at a radiant exposure that ranges from 0.5 J/cm$^2$ to 60 J/cm$^2$ during an irradiation session. The pulsed blue and/or red light may be applied one time (i.e., single irradiation session) or may be provided multiple times (i.e., multiple irradiation sessions) at the desired irradiance and radiant exposure.

Additional aspects of the invention, together with the advantages that are appurtenant thereto, are set forth in part in the description provided below, and in part will become apparent to those skilled in the art upon examination of the description or from the practice of the invention.

BRIEF DESCRIPTION OF THE DRAWINGS

Various exemplary embodiments of the present invention are described in detail below with reference to the attached drawing figures, wherein.

DETAILED DESCRIPTION OF EXEMPLARY EMBODIMENTS

I. General Overview

Figure 1A:
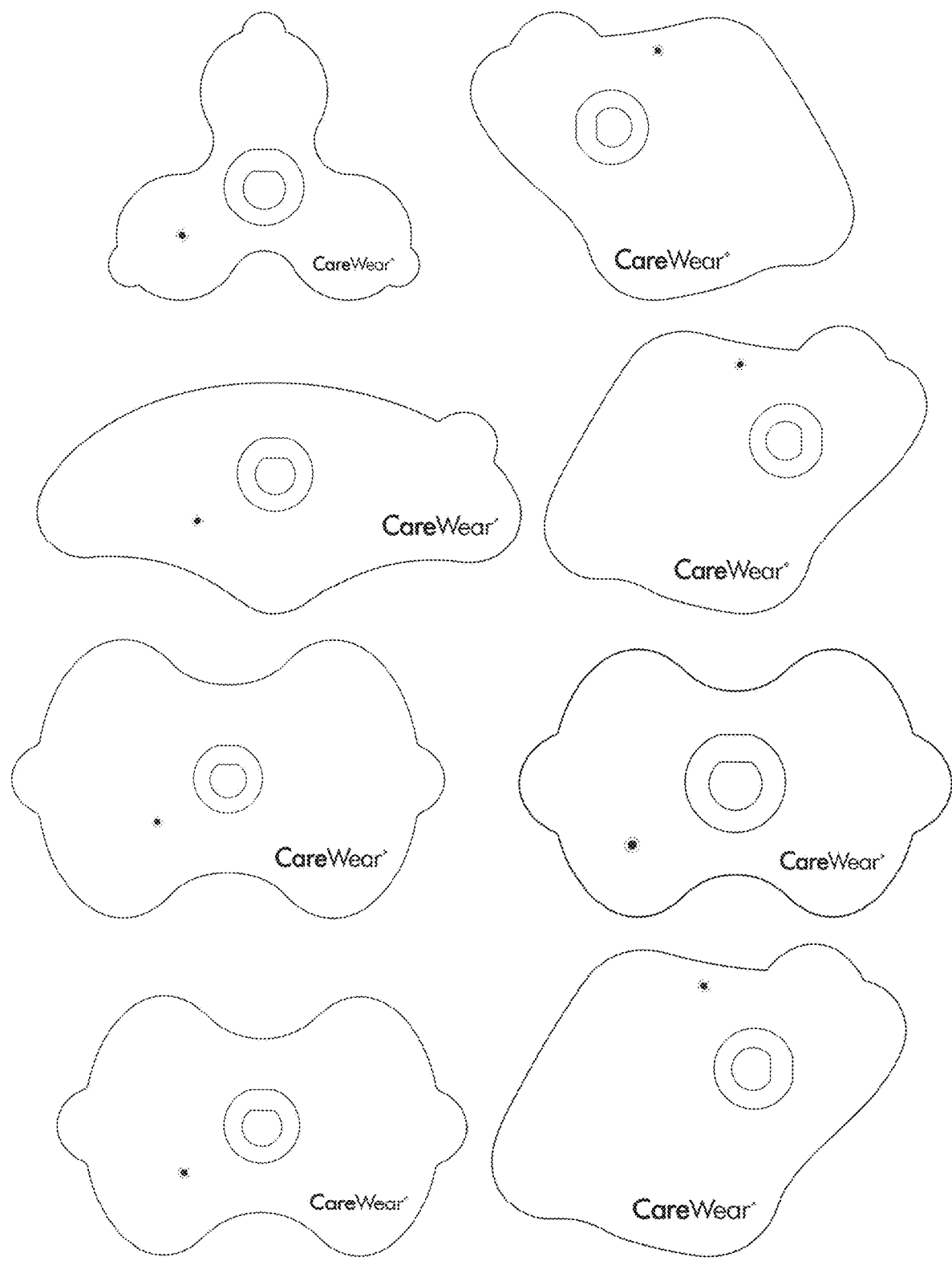
FIGS. 1A and 1B illustrate various exemplary shapes of light sources that are suitable for use in accordance with the present invention.

The method and system of the present invention may be used to irradiate tissue of a subject with pulsed blue and red light (or only pulsed blue light) at specified pulse parameters, dosages and time intervals, as described below, in order to reduce muscle fatigue, enhance wound healing and tissue repair, and reduce pain. As used herein, "blue light" refers to light having a wavelength ranging from about 380 nm to about 560 nm (e.g., 380, 390, 400, 410, 420, 430, 440, 450, 460, 470, 480, 490, 500, 510, 520, 530, 540, 550, 560 nm or some value or range therebetween) and, thus, encompasses the violet, blue, cyan and green portions of the visible light spectrum. A particularly suitable blue wavelength is about 450 nm. Also, "red light" refers to light having a wavelength ranging from about 600 nm to about 830 nm (e.g., 600, 610, 620, 630, 640, 650, 660, 670, 680, 690, 700, 710, 720, 730, 740, 750, 760, 770, 780, 790, 800, 810, 820, 830 nm or some value or range therebetween). A particularly suitable red wavelength is about 640 nm or 645 nm.

In one aspect of the invention, a light source is used to irradiate tissue with pulsed blue and red light in order to reduce muscle fatigue in a subject. In use, the light source is generally placed on the skin directly over the belly of the muscle to be treated and the muscle innervation, i.e., the motor point. The underlying tissue is then irradiated with pulsed blue and red light at specified pulse parameters, dosages and time intervals. The light treatment may be used to reduce muscle fatigue caused by strenuous activity or exercise. Athletes, for example, would particularly benefit from the light treatment when applied during a sporting event. Of course, it should be understood that any muscle or muscle group may be treated to reduce muscle fatigue in accordance with the present invention, including quadriceps, hamstrings, triceps surae, anterior tibias, abdominal muscles, erector spine muscles, muscles of the core, biceps, triceps, wrist extensors, shoulder musculature, upper, lower and mid back postural muscles, neck extensor/flexors, masseter and facial muscles, trapezius, elevator scapula, and intrinsic muscles of the toes and fingers.

In another aspect of the invention, a light source is used to irradiate tissue of a subject with pulsed blue and red light in order to enhance wound healing and tissue repair and reduce pain associated with various types of tissue injuries. In use, the light source is generally placed on the skin directly over the injured tissue. For example, the light source may be placed over an area where a muscle contusion has occurred or where a muscle, ligament or tendon has been stretched or torn. The light source can also be placed directly over an open skin wound or on a transparent wound dressing. The underlying tissue is then irradiated with pulsed blue and red light at specified pulse parameters, dosages and time intervals. The light treatment may be used to enhance healing of the injured tissue and also provide a decrease in pain caused by the injured tissue.

In yet another aspect of the invention, the light source is used to reduce muscle fatigue, enhance wound healing and tissue repair, and reduce pain, as described above, by irradiating the tissue with pulsed blue light at specified pulse parameters, dosages and time intervals. In this case, the pulsed red light is not used.

In accordance with the invention, the blue and red light (or only blue light) is applied to the tissue in a pulsed mode of irradiation. In general, the pulses have a pulse duration that ranges from about 5 microseconds to about 1,000 microseconds, and the off time between pulses ranges from about 10 microseconds to about 1 second. A suitable combination may range from about 5 microseconds to about 30 microseconds for the pulse duration with off times ranging from about 10 microseconds to about 100 microseconds. A particularly suitable combination provides a pulse duration of about 10 microseconds and an off time of about 20 microseconds. The pulses provided can each be a square wave, rectified sinusoidal waveform or any combination thereof, although other pulse shapes may also be used in accordance with the present invention. A square wave with a rise time of less than 1 microsecond is preferred. A particularly suitable pulse repetition rate ranges from about 33 kHz to about 40 kHz.

Preferably, the pulsed blue and red light has an average irradiance that ranges from about 0.1 mW/cm$^2$ to about 20 mW/cm$^2$, with an average irradiance of about 1 mW/cm$^2$ to about 5 mW/cm$^2$ being preferred at the skin or tissue surface. The peak irradiance in pulsed mode is about 3 times the average irradiance, i.e., about 0.3 mW/cm$^2$ to about 60 mW/cm$^2$ or the preferred range of about 3 mW/cm$^2$ to about 15 mW/cm$^2$ at a duty factor of 33%. At other duty factors, the peak irradiance may be higher or lower so that the average irradiance stays within the preferred ranges of irradiance described herein. The duty factor is typically in the range of about 20% to about 33%. The pulsed blue and/or red light is preferably provided at radiant exposures that range from about 0.5 J/cm$^2$ to about 60 J/cm$^2$, with a preferred range of about 2.5 J/cm$^2$ to about 30 J/cm$^2$, and a more preferred range of about 3.6 J/cm$^2$ to about 5 J/cm$^2$.

It should be understood that the low levels of light used in connection with the present invention (e.g., average irradiances of about 1 mW/cm$^2$ to about 5 mW/cm$^2$ and radiant exposures of about 3.6 J/cm$^2$ to about 5 J/cm$^2$) are very safe to the eye and meet international blue light safety requirements, including IEC TR 62778:2014 (Application of IEC 62471 for the assessment of blue light hazard to light sources and luminaries), IEC 62471:2006 (Photobiological safety of lamps and lamp systems), IEC 60601-2-57:2011 (Medical Electrical equipment—Part 2-57: Particular requirements for the basic safety and essential performance of non-laser light source equipment intended for therapeutic, diagnostic, monitoring and cosmetic/aesthetic use). This provides a significant advantage over continuous wave (CW) light sources that deliver light at high irradiances and radiant exposures.

The pulsed blue and red light (or only pulsed blue light) may be applied one time (i.e., single irradiation session) or may be provided multiple times (i.e., multiple irradiation sessions) at the desired irradiance and radiant exposure. One skilled in the art will appreciate that the irradiation time for each irradiation session is dependent on the dose, and is typically in the range of about 20 minutes to about 45 minutes for the irradiances and radiant exposures used in connection with the present invention.

Preferably, the pulsed blue and/or red light is applied during a plurality of irradiation sessions at pre-defined time intervals in accordance with an irradiation schedule. In certain embodiments, the irradiation sessions are repeated at daily intervals on two, three, four or more days. For example, in order to reduce muscle fatigue and enhance performance, an irradiation session may be scheduled prior to exercise or sports activity and/or after exercise or sports activity on a daily basis. As another example, in order to enhance would healing and tissue repair, the irradiation sessions may be scheduled immediately after the tissue injury and on a daily or twice daily basis thereafter until the tissue is repaired. Of course, other irradiation schedules that are suitable for a particular application may also be used within the scope of the present invention.

In addition to the basic pulsing of blue and/or red light as described above, the pulses may be further modulated with a low frequency signal timed to coincide with the heart rate or at a rate similar to the heart rate (i.e., 0.5 to 2 Hz or a multiple or harmonic thereof). This signal allows for recharge of the free oxygen from blood flow during the resting period of the photo stimulation. Duty factors in the range of 5% to 95% may be used for this modulation.

The application of pulsed blue light in combination with pulsed red light provides many beneficial effects that together reduce muscle fatigue, enhance wound healing and tissue repair, and reduce pain.

For example, the pulsed blue light stimulates nitric oxide release in mitochondria subject to inflammation, restoring mitochondrial respiration and increasing local vasodilation. The pulsed blue light also stimulates opsin receptors in the skin that are believed to be involved in pain management due to neuromodulation. These opsin receptors also have a role in tissue calcium release, wherein calcium has a vital function during muscle function and wound healing. The pulsed blue light further stimulates flavins, which are biological chromophores that repair damaged DNA, and also exerts anti-bacterial effects. Of course, it should be understood that the beneficial effects of pulsed blue light may be achieved with or without the use of pulsed red light.

The pulsed red light enhances anti-inflammatory effects and also increases the metabolism of the mitochondria to thereby increase the availability of adenosine triphosphate (ATP). Specifically, the pulsed red light stimulates cytochrome C oxidase, the terminal enzyme in the electron transport chain within the mitochondria, leading to increased enzyme activity, oxygen consumption, and ultimately greater ATP production. This improves muscle strength and endurance and accelerates healing by increasing the metabolic rate of fibroblasts (to thereby produce more collagen) and other cells associated with tissue repair. The pulsed red light further causes a dissociation of nitric oxide found during oxidative stress conditions. The dissociation of nitric oxide leads to less reactive oxidative species and less tissue damage when in a stressed state, thereby improving recovery time.

Thus, the combination of pulsed blue light with pulsed red light has synergistic effects on increasing blood flow, reducing inflammation, providing bacterial kill, and accelerating tissue repair, which are particularly effective in wound healing.

The application of blue and/or red light in a pulsed mode of irradiation provides several advantages over photobiomoulation techniques that utilize continuous wave (CW) light. For example, the delivery of light in CW mode has higher fluence requirements compared to pulsed modes. Because cells can only absorb light at certain rates, a certain amount of energy is converted to heat if the irradiance is too high. By contrast, pulsed modes enable the energy delivery to substantially match the cellular absorption rate. In addition, pulsed light excites chromophores for a long enough period of time to move the molecule to a singlet energy state. The pulse then turns off and the excited molecule returns to a triplet and then ground state. This allows more efficient energy transfer and is believed to cause free radical production triggering various beneficial cellular responses. With CW mode, the chromophores are maintained in an excited state and fewer go back to a ground state (they do so randomly as opposed to a cascade that follows the pulsing) and, thus, the effect of the light is reduced.

It should be noted that other wavelengths of light could also be produced by the light source, such as yellow, orange, and near infrared. These wavelengths may selectively target additional chromophores involved in pain management, tissue repair and enhanced muscle and neurological performance. Application of light to the skin at various wavelengths may also impact retiming of the circadian rhythm during global travel.

Figure 1B:
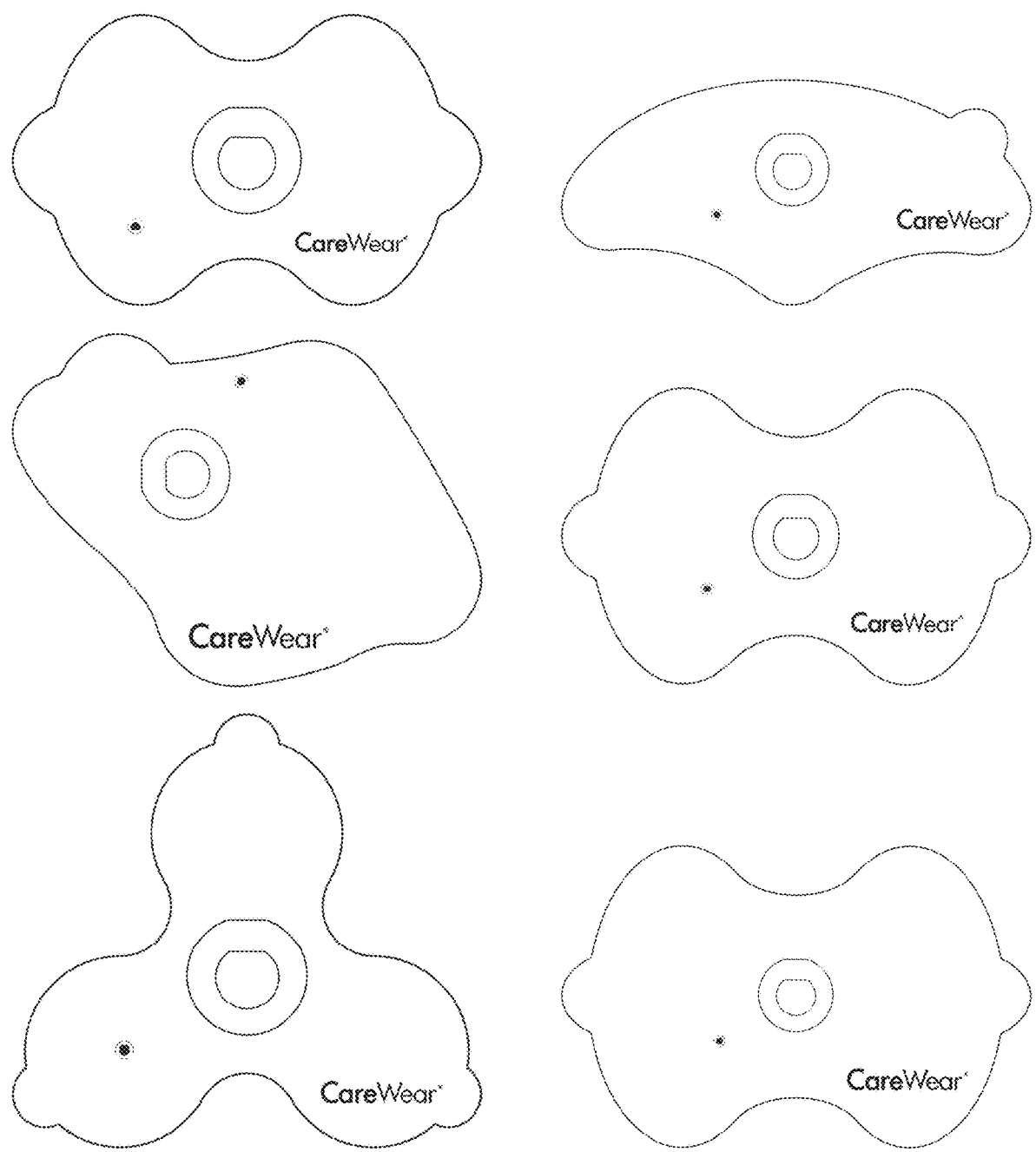

Any suitable light source may be used to apply the pulsed blue and red light (or only pulsed blue light) in accordance with the present invention. In some embodiments, the pulsed blue and/or red light is applied using a flexible light source in the form of a patch, pad, mask, wrap, fiber, or bandage, which is able to contact and conform to the skin or tissue surface to which it is applied in order to maximize optical coupling. The light source may have a variety of shapes and sizes. For example, the light source may be square, rectangular, circular, butterfly-shaped, elliptical, clover-shaped, oblong, crescent/moon-shaped, or any other shape that is suitable for a particular application. Examples of suitable light sources are generally illustrated in FIGS. 1A and 1B. The overall surface area of one side of the light source may range from, for example, 1 cm$^2$ to 1 m$^2$, although typically the surface area is about 1 to 2000 cm$^2$ (e.g., about 1, 4, 9, 16, 25, 36, 49, 64, 81, 100, 121, 144, 169, 196, 225, 289, 324, 361, 400, 441, 484, 529, 576, 625, 676, 729, 784, 841, 900, 961, 1024, 1089, 1156, 122, 1296, 1369, 1444, 1521, 1600, 1681, 1764, 1849, 1936 or 2000 cm$^2$ or some value therebetween). The light source is thus well adapted to be applied to various areas of the subject's body. Exemplary light sources are described in greater detail below.

An electronic circuit is programmed to control the light source so that the blue and red light (or only blue light) is provided in a pulsed mode of irradiation at desired levels of irradiance and radiant exposure. In some embodiments, the electronic circuit includes a microcontroller that provides a preprogrammed sequence of blue and/or red light pulses at a fixed dose during the irradiation session. In other embodiments, the electronic circuit additionally includes one or more sensors that operate in a closed loop to provide feedback to the microcontroller so as to dynamically control the dose during the irradiation session. Exemplary electronic circuits for both preprogrammed control and dynamic control of a light source are described in greater detail below.

II. Exemplary Light Sources

Various types of light sources may be used to provide the pulsed blue and red light (or only pulsed blue light) in accordance with the present invention. Exemplary light sources include printed light emitting diodes (printed LEDs) and organic light emitting diodes (OLEDs), either of which can be used in combination with quantum dots (QDs) as described below. Other suitable light sources include various types of lasers, light emitting diodes (LEDs) including micro LEDs that can be applied to a flexible substrate, polymer light emitting diodes (PLEDs) also known as light emitting polymers (LEPs), quantum dot LEDs (QLEDs), phosphorescent OLEDs, and fluorescent tubes emitting light in the blue and/or red spectral region.

A preferred light source is provided in the form of a very thin layered structure. An example of this type of light source is shown generally as reference numeral 10 in FIG. 2. Light source 10 is comprised of a plurality of layers 12 including a flexible light emitter 40 located between a flexible anode 50 and a flexible cathode 60. A suitable power source may be connected to anode 50 and cathode 60 to power the light source. Light source 10 is substantially planar in its form, although it is preferably flexible and is more preferably conformable such that it may conform to the contours of the subject's body. The overall thickness of light source 10 is typically about 10 mm or less (e.g., about 10, 9, 8, 7, 6, 5, 4, 3, 2, 1, 0.5, 0.4, 0.3, 0.2, 0.1, 0.05 mm or less).

Light source 10 produces light with an intensity that is substantially constant across the surface of the device so as to provide a substantially uniform light emission. As described in more detail below, flexible light emitter 40 may have a variety of different configurations for providing the pulsed blue and/or red light. It can be appreciated that light source 10 is capable of decreasing hot spots on the skin or tissue surface of a subject to provide a safer delivery of light. Also, a substantially uniform dose of light across the surface of the device ensures that all of the skin or tissue is effectively treated with the same dose of light.

Figure 3:
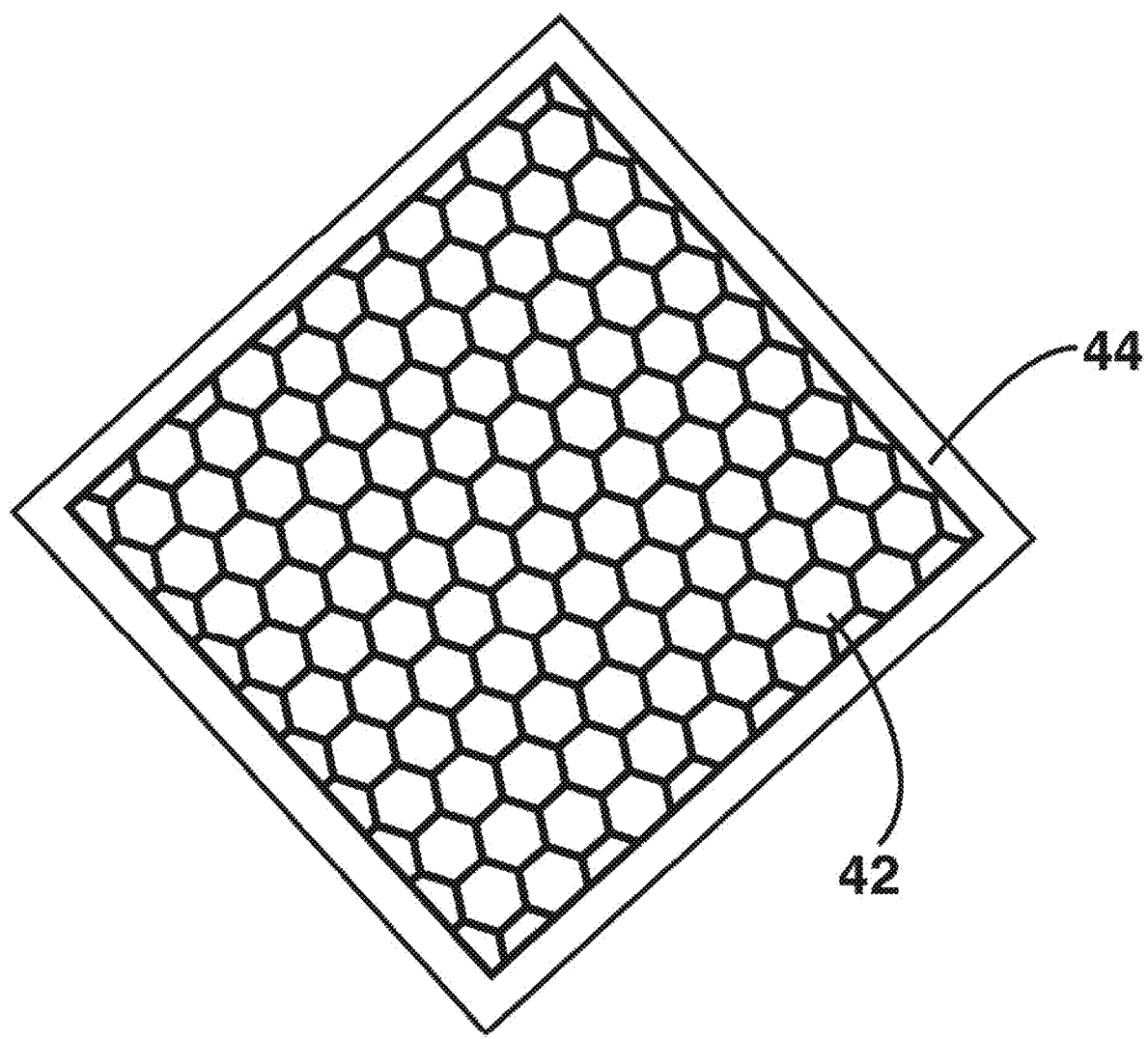
FIG. 3 illustrates a plurality of light emitting diodes printed on a flexible film (i.e., a printed LED film) that is suitable for incorporation into the light source shown in FIG. 2.

In some embodiments, flexible light emitter 40 comprises a printed LED film either by itself or in combination with a quantum dot film. An example of the printed LED film is shown in FIG. 3, which includes a plurality of light emitting diodes 42 printed on a flexible film 44. In this embodiment, the light emitting diodes 42 are printed in hexagon-shaped LED clusters at a density of 2.5 LEDS/mm$^2$. Of course, the LED clusters could have other shapes, the LEDS could be printed across the entire surface of the film, and/or the LEDs could be printed in other densities in accordance with the present invention.

In one embodiment, flexible light emitter 40 comprises a printed LED film that is laminated to a quantum dot film. In this embodiment, all of the light emitting diodes of the printed LED film (such as light emitting diodes 42 shown in FIG. 3) are configured to emit blue light. The quantum dot film comprises a slurry of quantum dots (including cadmium-free quantum dots (CFQDs)) coated on a flexible film and then another flexible film is placed thereon in order to seal the quantum dots between the two films. Alternatively, the CFQDs could be coated on the printed LED substrate with a barrier coating or film applied to the outer side in order to prevent oxidation of the CFQDs. The quantum dots are configured to convert blue light to red light upon receipt of the pulsed blue light from the printed LED film so as to maintain the same pulse characteristics for both the red and blue light. Various densities of quantum dots can be used to control the percentage of light converted from blue light to red light. In one embodiment, the percentages of blue and red light range from 20% blue light/80% red light to 80% blue light/20% red light. Of course, other percentages of blue and red light could also be used as desired for a certain application. Preferably, the blue light emitting diodes and the quantum dots are evenly distributed across the surface of the device so as to provide a substantially uniform emission of blue and red light.

In another embodiment, flexible light emitter 40 comprises only a printed LED film (i.e., a quantum dot film is not used in this embodiment). In this embodiment, the light emitting diodes of the printed LED film (such as light emitting diodes 42 shown in FIG. 3) comprise a combination of blue and red light emitting diodes that are printed on a flexible film (such as flexible film 44 shown in FIG. 3) in a checkerboard or grid-like pattern. The respective number of blue and red light emitting diodes can be chosen to achieve the desired levels of blue and red light. In one embodiment, the percentages of blue and red light preferably range from 20% blue light/80% red light to 80% blue light/20% red light. Of course, other percentages of blue and red light could also be used as desired for a certain application. Preferably, the blue and red light emitting diodes are evenly distributed across the surface of the device so as to provide a substantially uniform emission of blue and red light.

It should be understood that the irradiance and radiant exposure of each of the blue light and red light will be a percentage of the total irradiance and radiant exposure discussed above, as determined by the density of the quantum dots (for the first embodiment discussed above) or the respective numbers of blue and red light emitting diodes (for the second embodiment discussed above), or the drive current applied respectively to the blue and red light emitting diodes by the driving device. As such, the desired levels of blue light and red light may be selectively achieved for a particular light treatment.

In another embodiment, flexible light emitter 40 comprises OLEDs laminated to a quantum dot film, wherein the OLEDs emit blue light and the quantum dot film converts a portion of the blue light to red light. In yet another embodiment, flexible light emitter 40 comprises OLEDS that emit both blue and red light. It can be appreciated that these embodiments are similar to the two embodiments described above, with the exception that the printed LED film is replaced with the OLEDs. In yet other embodiments, flexible light emitter 40 comprises printed LED film or OLEDS that emit only blue light.

Figure 2:
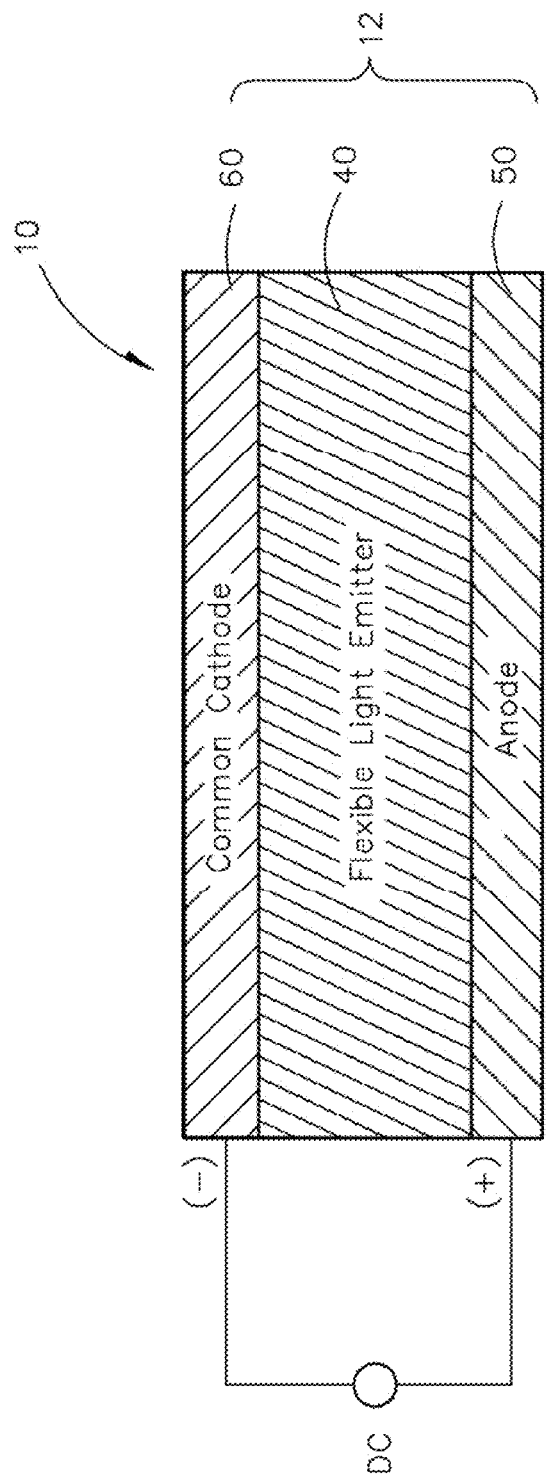
FIG. 2 illustrates the general structure of a light source for delivering pulsed blue and/or red light in accordance with the present invention, wherein the light source includes a flexible light emitter positioned between a cathode and an anode.
Figure 4:
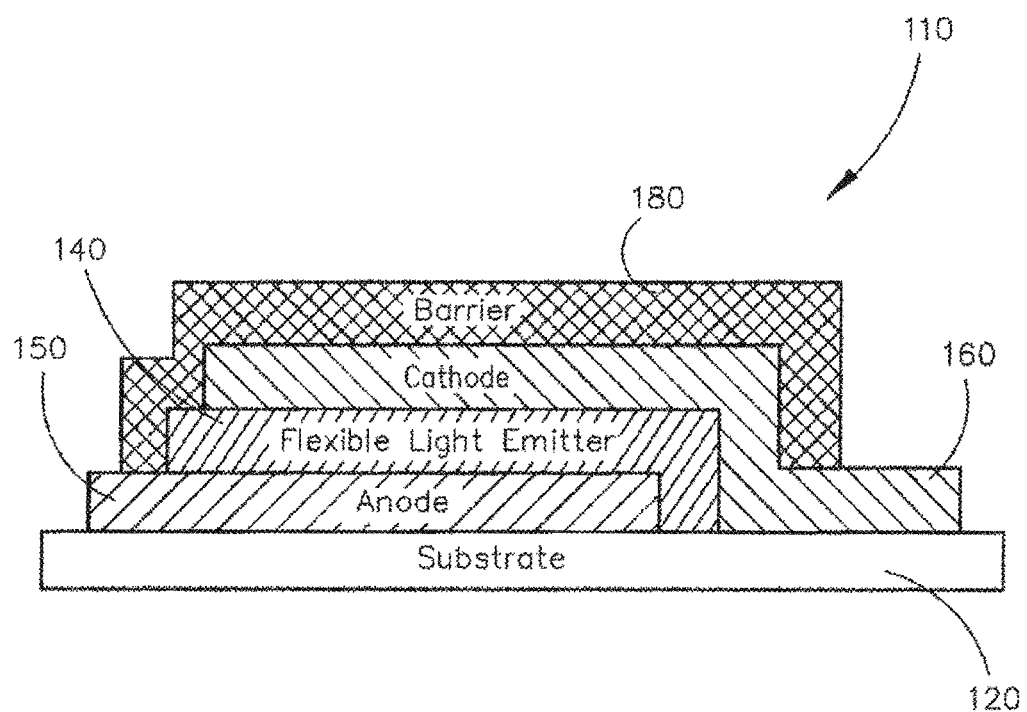
FIG. 4 illustrates a light source with a bottom light emitting configuration that is suitable for delivering pulsed blue and/or red light in accordance with the present invention.
Figure 5:
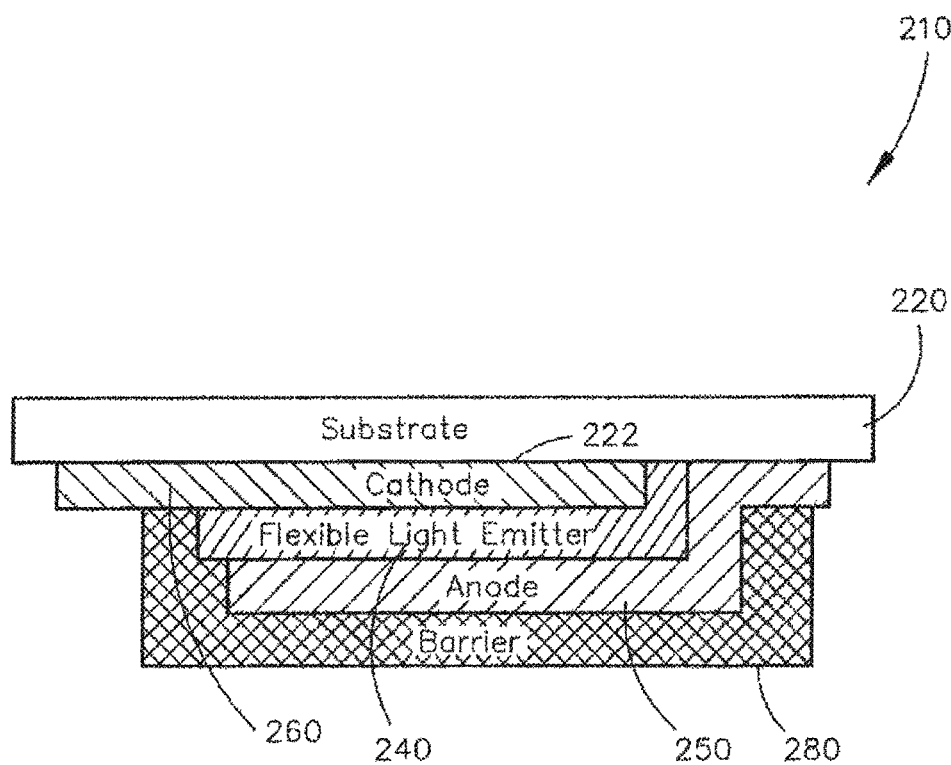
FIG. 5 illustrates a light source with a top light emitting configuration that is suitable for delivering pulsed blue and/or red light in accordance with the present invention.

Referring now to FIGS. 4 and 5, the layers of light source 10 shown in FIG. 2 may be adapted to have a "bottom" light emitting configuration or a "top" light emitting configuration.

FIG. 4 illustrates an exemplary light source 110 with a "bottom" light emitting configuration. Light source 110 comprises a flexible light emitter 140 located between a flexible anode 150 and a flexible cathode 160, all of which are formed on a transparent substrate 120. A power source no shown) may be connected to anode 150 and cathode 160 to power the light source. Further, a transparent barrier layer 180 protects flexible light emitter 140 from moisture and oxygen. In this embodiment, both substrate 120 and anode 150 are transparent. Light generated from flexible light emitter 140 is emitted through anode 150 and substrate 120 such that the device has a "bottom" light emitting configuration. A layer of hydrogel is preferably used as an adhesive to adhere the light source to the skin or tissue surface of the subject to thereby provide optical light piping and maximize optical coupling (i.e., the hydrogel has an index of refraction that substantially matches the indices of refraction of the light source and the skin or tissue surface of the subject). Alternatively, a transparent adhesive film such as a silicone film or pressure sensitive adhesive (PSA) may be used in place of the hydrogel.

FIG. 5 illustrates an exemplary light source 210 with a "top" light emitting configuration. Light source 210 comprises a flexible light emitter 240 located between a flexible anode 250 and a flexible cathode 260, all of which are formed on a bottom surface 222 of a substrate 220 (i.e., the surface facing towards a surface to be irradiated). A power source (not shown) may be connected to anode 250 and cathode 260 to power the light source. Further, a transparent barrier layer 280 protects the flexible light emitter 240 from moisture and oxygen. In this embodiment, cathode 260 is highly reflective to the light generated by flexible light emitter 240 such that the light is directed towards the surface to be irradiated. Both anode 250 and barrier layer 280 are transparent. Light generated from flexible light emitter 240 is emitted through anode 250 and barrier layer 280 such that the device has a "top" light emitting configuration. A layer of hydrogel or a transparent adhesive film such as a silicone film or pressure sensitive adhesive (PSA) is preferably used as an adhesive to adhere the light source to the skin or tissue surface of the subject to thereby provide optical light piping and maximize optical coupling as described above.

The various elements/layers of the light sources shown in FIGS. 4 and 5 will now be described in greater detail.

Substrate

The light source comprises a substrate that is capable of supporting the various other layers of the light source. The substrate is preferably flexible and/or conformable to the contours of a subject's body. The substrate can comprise, for example, an inorganic material, an organic material, or a combination of inorganic and organic materials. The substrate may be, for example, made from metals, plastics or glass. The substrate may be any shape to support the other components of the light source, for example, the substrate may be substantially flat or planar, curved, or have both substantially flat and curved portions. Ideally, the substrate is formed of a material that is a latex-free, non-toxic, non-allergenic, and resistant to UV, sunlight and most infection control products.

In some embodiments, the substrate is transparent. As used herein, the term "transparent" generally means transparency for light and includes both clear transparency as well as translucency. Generally, a material is considered transparent if at least about 50%, preferably about 60%, more preferably about 70%, more preferably about 80% and still more preferably about 90% of the light illuminating the material can pass through the material. In contrast, the term "opaque" generally refers to a material in which the light is substantially absorbed or reflected, e.g., at least 90% of the light is absorbed or reflected, and typically at least 95% of the light is absorbed or reflected.

In some embodiments, the substrate may be comprised of a silicon-based material, rubber, thermoplastic elastomers (TTP), or other polymeric material, such as polyester, polyethylene terephthalate (PET), polyethylene naphthalate (PEN), polycarbonate, polystyrene, polyacryl, polyether sulfone (PES), etc. Transparent substrates may include, for example, polyethylene, ethylene-vinyl acetate copolymers, polyimide (PI), polyetherimide (PEI), ethylene-vinyl alcohol copolymers, polypropylene, polystyrene, polymethyl methacrylate, PVC, polyvinyl alcohol, polyvinylbutyral, polyether ether ketone, polysulfone, polyether sulfone, as well as fluoropolymers, such as, fluorinated ethylene-propylene (FEP), tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyester, polycarbonate, polyurethanes, polyimide or polyether imide.

In another embodiment, the transparent substrate is a polyester film, such as Mylar. In another aspect, the substrate comprises a polyetheretherketone film commercially available from Victrex under the name APTIV. In still another aspect, the substrate is a thin film sold under the name Flexent by Konica Minolta or flexible glass such as Willow Glass by Dow Corning. Ideally, substrates in direct or indirect contact with organic layers will have exceptional barrier capabilities that withstand heat, offer flexibility, have sustained reliability and can be mass produced.

Conductive Layers (Anode and Cathode)

The light source comprises a plurality of conductive layers (i.e., electrodes), namely, a cathode and an anode. The anode may comprise, for example, a transparent conductive oxide (TCO), such as, but not limited to, indium tin oxide (ITO), zinc oxide (ZnO), carbon nanotubes and the like. The cathode may also comprise, for example, a thin metal film or fibers such as aluminum, copper, gold, molybdenum, iridium, magnesium, silver, lithium fluoride and alloys thereof, or a non-metal conductive layer such as carbon nanofibers.

Because the light source must emit light through one or both electrodes, at least one of the electrodes must be transparent. The transparent electrode is positioned on the side of the light source designed to be facing the tissue to be irradiated. For a light source intended to emit light only through the bottom electrode (i.e., the surface-facing electrode), the top electrode (i.e., the electrode facing away from the surface) does not need to be transparent. The top electrode may thus comprise an opaque or light-reflective metal layer having a high electrical conductivity. Where a top electrode does not need to be transparent, using a thicker layer may provide better conductivity, and using a reflective electrode may increase the amount of light emitted through the transparent electrode by reflecting light back towards the transparent electrode. Fully transparent light sources may also be fabricated, where both electrodes are transparent. A flexible printed circuit board may be laminated to the top conductive layers to increase the conductivity of the top and/or bottom electrodes to allow the passage of a higher current than the printed materials may be able to conduct. This allows a higher peak optical output and reduces heat and resistive losses in the substrate.

The thickness of each electrode is typically about 5 micron or less (e.g., about 5, 4.5, 4, 3.5, 3, 2.5, 2, 1.5, 1 micron or less). In one embodiment, each electrode comprises 5 microns of silver with a laminate of 17 to 40 microns of copper.

The electrodes are preferably flexible in nature. In some embodiments, the conductive materials of one or both of the electrodes may include, but are not limited to, transparent conductive polymer materials, such as indium tin oxide (ITO), fluorine-doped tin oxide (FTO), ZnO—Ga2O3, ZnO—Al2O3, SnO2-Sb2O3, and polythiophene. In addition, the electrodes may be comprised of carbon nanotubes, silver or copper grids or bushbars plated on a transparent substrate or silver nanowires or nanoparticles deposited substrate with a poly(3,4-ethylenedioxythiophene) poly(styrenesulfonate) (PEDOT:PSS) coating. Additional conductive polymer layers may be added to improve conductivity.

In one aspect, the transparent conductive electrode may be carbon-based, for example, carbon nanotubes, carbon nanowires, graphene, and the like. One preferred electrode comprises graphene. While one or two layers of graphene are preferred, the electrode may comprise about 1 to 20 layers of graphene (e.g., 1, 2, 3, 4, 5, 6, 7, 8, 9, 10, 11, 12, 13, 14, 15, 16, 17, 18, 19, 20 layers or some range therebetween). The graphene electrode(s) also have the effect of protecting the photoactive layer sandwiched between them from oxidation. Therefore, environmental stability of the light source can be improved. The graphene electrode may optionally have a plurality of plasmonic nanostructures, which may have various morphologies (spherical, rods, discs, prisms, etc.). Exemplary nanostructures include those made of gold, silver, copper, nickel, and other transition metals, for example gold nanoparticles, silver nanoparticles, copper nanoparticles, nickel nanoparticles, and other transition metal nanoparticles. In general, any electrically conductive materials, such as oxides and nitrides, of surface plasmonic resonance frequencies in the visible spectrum can be made into plasmonic nano structures for the same purpose. In some embodiments, the plasmonic particles have the size of about 1 nm to about 300 nm (e.g., about 10, 50, 100, 150, 200, 250, 300 nm, or some range therebetween).

Light Emitter

The light source includes a light emitter, as generally described above. The thickness of the light emitter is preferably about 2 mm or less (e.g., about 2, 1.8, 1.6, 1.4, 1.2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01 mm or less). Most preferably, the light emitter is about 10 to 200 nm in thickness (e.g., about 200, 180, 160, 140, 120, 100, 90, 80, 70, 60, 50, 40, 30, 20, 10 nm, or some range therebetween). In one embodiment, the light emitter comprises micro LEDS having a thickness of approximately 10-30 microns, which are applied to a flexible substrate or a flexible printed circuit board. In other embodiments, the light emitter comprises a printed LED film or OLEDs either of which can be used in combination with a quantum dot film, as described in greater detail below. The light emitter is preferably flexible and emits light in response to an electric current applied to the anode and cathode.

Printed LEDs

In some embodiments, the light emitter may include printed LEDs (organic or inorganic), i.e., LED ink. With LED ink, each light source is very small which enables the LEDs to be positioned in very close proximity to each other. During fabrication, the LEDs may be printed in a uniform manner whereby each LED operates as a point source in which the beams from the individual LEDs are substantially parallel to each other to provide substantially uniform light across the surface of the device. Unlike conventional LEDs, printed LEDs do not need to be positioned a sufficient distance from the surface to be irradiated in order to deliver a substantially uniform dose of light. There are several known methods for printing such LEDs, as described below.

In one method, a plurality of individual LEDs are suspended and dispersed in a liquid or gel comprising one or more solvents and a viscosity modifier so as to form a diode ink that is capable of being printed on a flexible substrate or a flexible printed circuit board (e.g., through screen printing, flexographic printing and the like). In one aspect, the average surface area concentration of LEDs is from about 25 to 50,000 LEDs per square centimeter. In general, each LED includes a light emitting region, a first metal terminal located on a first side of the light emitting region, and a second metal terminal located on a second side of the light emitting region. The first and second metal terminals of each LED may be electrically coupled to conductive layers (i.e., electrodes) to enable the light emitting region to emit light when energized. A flexible printed circuit board may be laminated to the top conductive layers or the diode ink may be printed on a flexible printed circuit board to increase the conductivity of the top and/or bottom electrodes to allow the passage of a higher current than the printed materials may be able to conduct. This allows a higher peak optical output and reduces heat and resistive losses in the substrate.

Figure 6:
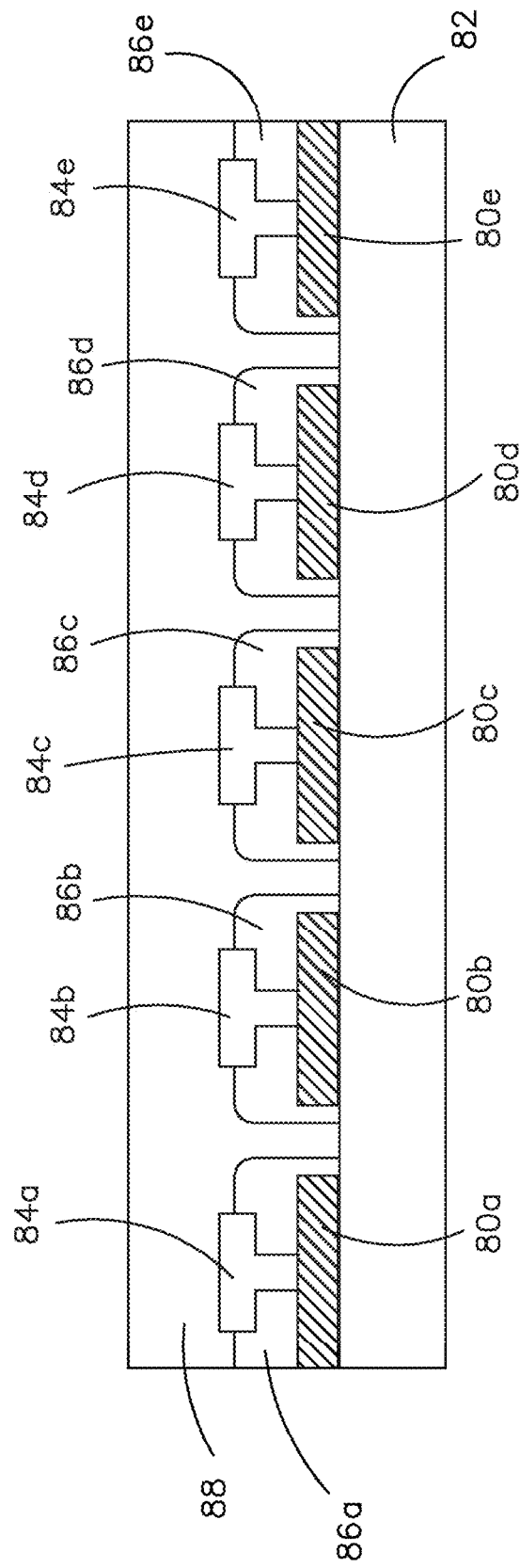
FIG. 6 illustrates an exemplary printed LED structure.

An exemplary printed LED light source is shown generally in FIG. 6, wherein only five LEDs are provided in order to simplify the description. As can be seen, this device includes a plurality of conductors 80a-80e deposited on a flexible substrate 82. A plurality of LEDs 84a-84e are deposited on the conductors 80a-80e such that the first metal terminals of the LEDs 84a-84e are electrically coupled to the conductors 80a-80e. One skilled in the art will appreciate that the LEDs 84a-84e may be formed of various shapes. Preferably, the LEDs 84a-84e settle into a position over conductors 80a-80e such that they maintain their polarity based on the shape of the LEDs. Next, a plurality of dielectric layers 86a-86e are deposited over the LEDs 84a-84e and the conductors 80a-80e, as shown. Another conductor 88 is then deposited over the LEDs 84a-84e and dielectric layers 86a-86e such that the second metal terminals of the LEDs 84a-84e are coupled to the conductor 88. One skilled in the art will appreciate that the substrate 82 and conductors 80a-80e may be transparent so that light is emitted from the bottom of the device and/or conductor 82 may be transparent so that light is emitted from the top of the device. Various configurations of printed LEDs that may be manufactured in accordance with the above method are described in Lowenthal et al., U.S. Pat. No. 8,415,879.

In another method, the light source comprises LEDs that are created through a printing process. In this method, a substrate is provided that includes a plurality of spaced-apart channels. A plurality of first conductors are formed on the substrate such that each first conductor is positioned in one of the channels. Next, a plurality of substantially spherical substrate particles are coupled to the first conductors and, then the substantially spherical substrate particles are converted into a plurality of substantially spherical diodes. The substantially spherical diodes may comprise, for example, semiconductor LEDs, organic LEDs encapsulated organic LEDs, or polymer LEDs. A plurality of second conductors are then formed on the substantially spherical diodes. Finally, a plurality of substantially spherical lenses suspended in a polymer (wherein the lenses and suspending polymer have different indices of refraction) are deposited over the substantially spherical diodes and the second conductors. Thus, in this method, the LED's are built up on the substrate as opposed to being mounted on the substrate. Various configurations of printable LEDs that may be manufactured in accordance with the above method are described in Ray et al., U.S. Pat. No. 8,384,630.

Quantum Dots

In some embodiments, the light emitter may also include quantum dots positioned between the light emitting surface and the tissue to be irradiated in order to convert all or a portion of the light emission into a different wavelength. The quantum dots may contain cadmium or may be organic and cadmium-free. Various densities of quantum dots can be used to control the percentage of light converted from one wavelength to another. The wavelength is typically down converted to a longer wavelength (Stokes conversion). For example, blue light at 450 nm may be converted into red light at 630 nm. Thus, wavelength conversion provides an additional wavelength (e.g., red) from a fixed wavelength source (e.g., blue).

A slurry of quantum dots (including cadmium-free quantum dots (CFQDs)) may be coated on a flexible film and then another flexible film placed thereon in order to seal the quantum dots between the two films. One of the films preferably has an adhesive on its outer side to allow bonding to the printed LED film, as described above, or OLED film. Alternatively, the CFQDs could be coated on the printed LED film or OLED film with a barrier coating or film applied to the outer side in order to prevent oxidation of the CFQDs. As another alternative, encapsulated quantum dots may be embedded into the hydrogel used to connect the light source to the skin or tissue surface to be irradiated.

OLEDs

In some embodiments, the light emitter may include OLEDs such that the light emitter is a thin organic film. As used herein, the term "organic" with respect to OLEDs encompasses polymeric materials as well as small molecule organic materials that may be used to fabricate organic opto-electronic devices. Such materials are well known in the art. "Small molecule" refers to any organic material that is not a polymer, and it will be appreciated that "small molecules" may actually be quit large. "Small molecules" may include repeat units in some circumstances. For example, using a long chain alkyl group as a substituent does not remove a molecule from the "small molecule" class. "Small molecules" may also be incorporated into polymers, for example as a pendent group on a polymer backbone or as a part of the backbone. "Small molecules" may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a "small molecule" has a well-defined chemical formula with a single molecular weight, whereas a polymer has a chemical formula and a molecular weight that may vary from molecule to molecule.

Generally speaking, in the flexible light emitter, electrons and holes recombine to radiate photons. The radiative photon energy emitted from the flexible light emitter corresponds to the energy difference between the lowest unoccupied molecular orbital (LUMO) level and the highest occupied molecular orbital (HOMO) level of the organic material. Photons of lower energy/longer wavelength may be generated by higher-energy photons through fluorescent or phosphorescent processes.

As described below, the flexible light emitter may optionally include one or more of a hole injection material (HIM), a hole transport material (HTM), a hole blocking material (HBM), an electron injection material (EIM), an electron transport material (ETM), an electron blocking material (EBM), and/or an exciton blocking material (ExBM).

In one aspect, the emissive electroluminescent layer may include a hole injection material (HIM). A HIM refers to a material or unit capable of facilitating holes (i.e., positive charges) injected from an anode into an organic layer. Typically, a HIM has a HOMO level comparable to or higher than the work function of the anode, i.e., −5.3 eV or higher.

In another aspect, the emissive electroluminescent layer may include a hole transport material (HTM). A HTM is characterized in that it is a material or unit capable of transporting holes (i.e., positive charges) injected from a hole injecting material or an anode. A HTM has usually high HOMO, typically higher than −5.4 eV. In many cases, HIM can also function as HTM, depending on the adjacent layer.

In another aspect, the emissive electroluminescent layer may include a hole blocking material (HBM). A HBM generally refers to a material which, if deposited adjacent to an emitting layer or a hole transporting layer in a multilayer structure, prevents the holes from flowing through. Usually it has a lower HOMO as compared to the HOMO level of the HTM in the adjacent layer. Hole-blocking layers are frequently inserted between the light-emitting layer and the electron-transport layer.

In another aspect, the emissive electroluminescent layer may include an electron injection material (EIM). An EIM generally refers to a material capable of facilitating electrons (i.e., negative charges) injected from a cathode into an organic layer. The EIM usually has a LUMO level comparable to or lower than the working function of the cathode. Typically, the EIM has a LUMO lower than −2.6 eV.

In another aspect, the emissive electroluminescent layer may include an electron transport material (ETM). An ETM generally refers to a material capable of transporting electrons (i.e., negative charges) injected from an EIM or a cathode. The ETM has usually a low LUMO, typically lower than −2.7 eV. In many cases, an EIM can serve as an ETM as well, depending on the adjacent layer.

In another aspect, the emissive electroluminescent layer may include an electron blocking material (EBM). An EBM generally refers to a material which, if deposited adjacent to an emissive or electron transporting layer in a multilayer structure, prevents the electron from flowing through. Usually it has a higher LUMO as compared to the LUMO of the ETM in the adjacent layer.

In another aspect, the emissive electroluminescent layer may include an exciton blocking material (ExBM). An ExBM generally refers to a material which, if deposited adjacent to an emitting layer in a multilayer structure, prevents the excitons from diffusing through. ExBM should have either a higher triplet level or singlet level as compared to the emitting layer or other adjacent layer.

Exemplary OLED materials are described in Hammond et al., U.S. Published Patent Application No. 2010/0179469; Pan et al., U.S. Published Patent Application No. 2013/0006119; Buchholz et al., PCT Published Patent Application No. WO 2012/010238; and Adamovich et al., U.S. Published Patent Application No. 2007/0247061.

Figure 7:
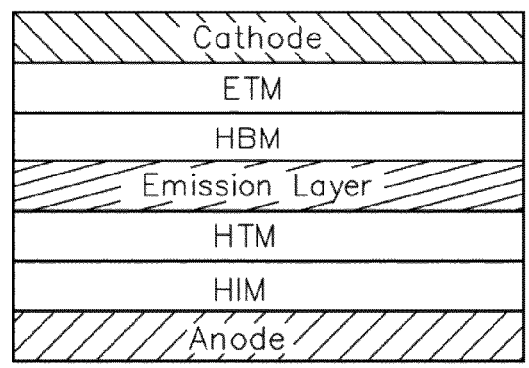
FIG. 7 illustrates an exemplary OLED structure.

Referring to FIG. 7, a typical sequence of materials found in the flexible light emitter between the anode and the cathode of the OLED is HIM, HTM, emission layer, HBM, and ETM. Another typical sequence of materials is HTM, emission layer, and ETM. Of course, other sequences of materials are also possible. Further, the OLED may comprise one or more interlayers.

In one aspect, the flexible light emitter comprises a single layer. The flexible light emitter may comprise, for example, a conjugated polymer which is luminescent, a hole-transporting polymer doped with electron transport molecules and a luminescent material, or an inert polymer doped with hole transporting molecules and a luminescent material. The flexible light emitter may also comprise an amorphous film of luminescent small organic molecules which can be doped with other luminescent molecules.

In another aspect, the flexible light emitter may comprise one or more different emissive materials in either the same emission layer or in different emission layers. For example, the flexible light emitter may comprise 5, 4, 3, 2, or 1 radiation emitting materials. The various different emissive materials may be selected from the emissive materials described in the references set forth above, but any other suitable emissive material can be employed. If two emissive materials are used in one emission layer, the absorption spectrum of one of the two emissive materials preferably overlaps with the emission spectrum of the other emissive material. The emissive materials may be arranged in stacked layers or side-by-side configurations. The emissive layer may comprise a continuous region forming a single emitter or a plurality of light emitters. The plurality of light emitters may emit light with substantially different wavelengths. The plurality of light emitters may be vertically stacked within the emissive layer or they may form a mixture. In some embodiments, a dopant is dispersed within an organic host matrix. In one embodiment, a layer of quantum dots is sandwiched between two organic thin films.

In another aspect, the flexible light emitter may comprise a plurality of layers sharing a common anode and/or cathode. In this case, individual layers are stacked one on top of another. The stacked configuration may generally include intermediate electrodes disposed between adjacent layers such that successive layers share an intermediate electrode, i.e., a top electrode of one layer is the bottom electrode of another in the stack. The stacked layers may be formed of different materials, and therefore, different emissions spectra.

The flexible light emitter may be substantially transparent. When mostly transparent layers are used, a plurality of emissive layers may be vertically stacked without substantially blocking light emission from individual layers. The flexible light emitter may comprise a single or multiple layers, for example, a combination of p- and n-type materials. The p- and n-type materials may be bonded to each other in the layer. The bonding may be ionic or covalent bonding, for example. The multiple layers of the flexible light emitter may form hetero structures therebetween.

The light source may optionally include a light dispersion layer, such as a micro-lens array. It has been found that one of the key factors that limits the efficiency of OLED devices is the inefficiency in extracting the photons generated by the electron-hole recombination out of the OLED devices. Due to the high optical indices of the organic materials used, most of the photons generated by the recombination process are actually trapped in the devices due to total internal reflection. These trapped photons never leave the OLED devices and make no contribution to the light output from these devices. In order to improve the extraction or outcoupling of light from OLEDs, the device may include an internal scattering layer of high index particles such as TiOx in a transparent photoresist or a micro-lens array (MLA) layer. Exemplary MLAs and methods for forming the same are described in Gardner et al., U.S. Published Patent Application No. 2004/01217702; Chari et al. U.S. Pat. No. 7,777,416; Xu et al., U.S. Pat. No. 8,373,341; Yamae et al., *High-Efficiency White OLEDs with Built-up Outcoupling Substrate*, SID Symposium Digest of Technical Papers, 43 694 (2012); and Komoda et al., *High Efficiency Light OLEDS for Lighting*, J. Photopolymer Science and Technology, Vol. 25, No. 3 321-326 (2012).

Barrier Layer

The light source may optionally include one or more encapsulation or barrier layers that isolate the light emitter (or other layers) from an ambient environment. The encapsulation or barrier layer is preferably substantially impermeable to moisture and oxygen. In general, the moisture and oxygen sensitive components should be enclosed by materials having gas permeation properties. The barrier preferably achieves low water vapor permeation rates of $10^{-4}$ $g/m^2/day$ or less, $10^{-5}$ $g/m^2/day$ or less, and even more preferably about $10^{-6}$ $g/m^2/day$ or less.

The encapsulation or barrier layer may be glass or a plastic, for example. Exemplary materials include a polyetheretherketone film commercially available from Victrex under the name APTIV. In still another aspect, the substrate is a thin film sold under the name Flexent by Konica Minolta or flexible glass such as Willow Glass by Dow Corning. Ideally, substrates in direct contact with organic layers will have exceptional barrier capabilities that withstand heat, offer flexibility, have sustained reliability and can be mass produced.

The light source may be further covered with a transparent or semi-transparent covering. The covering may provide comfort for a subject using the light source. The covering may provide protection to the light source, keeping dirt and fluid off of the device and providing a cushion to protect the device from impact.

Hydrogel or Adhesive Layer

In some embodiments, a transparent hydrogel or double-sided adhesive tape layer is applied to the light emitting surface of the light source to attach it to the skin or tissue surface of the subject. Alternatively, a transparent adhesive film such as a silicone film or pressure sensitive adhesive (PSA) may be used. This layer may be a single use disposable or, alternatively, this layer may be used multiple times in cases where there is no concern of contamination. The hydrogel or adhesive layers may also contain additional anti-bacterials. The double-sided transparent adhesive tape may be, for example, 3M 9964 Clear Polyester Diagnostic Microfluidic Medical Tape (3M.com). The silicone film may be, for example, an SSA200 or 250 film with a release film or layer available from Dow Chemical Company. Various hydrogels and adhesives are available based on the adhesion requirements for various skin types. The hydrogels and adhesives are designed to provide light piping between the light sources and the skin surface. The optical coupling of the emitters (printed LEDs, OLEDs, etc.) is optimized by matching the indeces of refraction of the hydrogel, the emitting substrates, and the skin. In addition, the hydrogels or adhesives may contain additional dispersion layers such as a fine mesh or lens to further distribute the light evenly throughout the tissue to be treated.

III. Control of Light Source

The light source described above is driven and controlled by an electronic circuit that includes, for example, a power supply, one or more drive circuits, and a control module. For flexible light sources, the electronic circuit may be provided in a separate housing electrically connected to the light source or may be built into the flexible material that mounts the light source.

The power supply may be any power supply capable of supplying sufficient power to activate the light source. The power supply may comprise a disposable or rechargeable battery, solar cell, fuel cell, an adapter, or may be powered by the power grid. The battery may be a printed battery, flexible lithium-ion primary or secondary cells, carbon nanotube, electrochemical inks, or other flexible organic or inorganic primary or secondary cells using non-toxic or limited toxicity materials. In some embodiments, the battery is roll-to-roll printed on the lamp substrate. The light source is preferably driven by direct current (DC) or pulsed DC. One skilled in the art will understand that the output voltages and current levels of the DC or pulsed DC control the peak output of the device, which in combination with the treatment time control the dose. In embodiments that utilize both blue light emitting diodes and red light emitting diodes printed in a checkerboard or grid-like pattern on a flexible film, as described above, it is possible to use separate power grids to more precisely control the dosage of the blue and red light.

Figure 8:
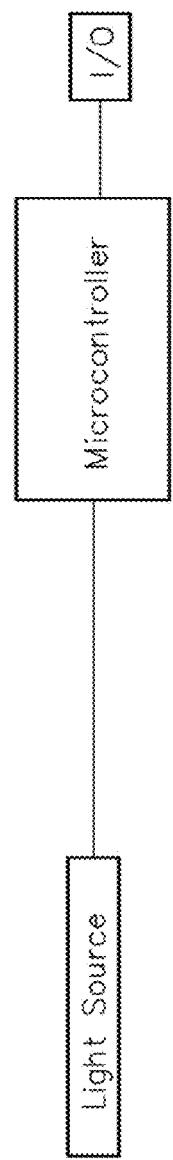
FIG. 8 is a block diagram of an electronic circuit for controlling a light source in accordance with the present invention, wherein the electronic circuit includes a microcontroller that is preprogrammed to provide a fixed dose of light.

FIG. 8 is a block diagram of an exemplary system in which the light source and light source drive circuit are controlled by a microcontroller in accordance with a pre-programmed treatment cycle that provides a sequence of light at a fixed dose for a specific treatment. The microcontroller may control the light source by adjusting the activation and deactivation of the light source, voltage, current, pulse width, duty factor, and light treatment time. One skilled in the art will appreciate that other operating parameters may also be controlled by the microcontroller in accordance with the present invention.

The microcontroller is also connected to one or more input/output (I/O) devices, such as an LED that provides an indication of whether the light source is on/off or an audio buzzer that alerts the user upon completion of a particular treatment. An on/off switch may also be provided to power the light source.

The system may be used in a number of treatment (irradiation) sessions that together result in an overall treatment time. For such cases, the microcontroller may include at least one timer configured to measure session time and overall treatment time or both. The timer may be used simply to monitor the session time or overall treatment time or may be used to deactivate the light source after completion of a session or overall treatment. A real time clock associated with the system can monitor the treatments and track/manage treatment sequences and dosing.

Figure 9:
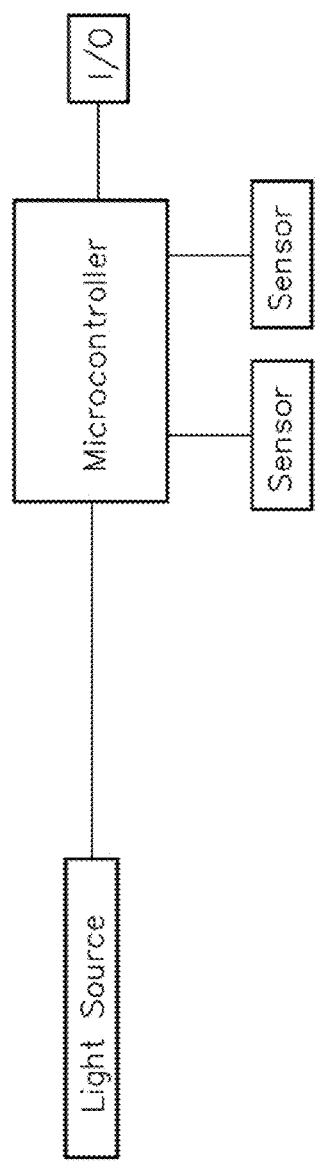
FIG. 9 is a block diagram of an electronic circuit for controlling a light source in accordance with the present invention, wherein the electronic circuit includes sensors that operate in a closed loop to provide feedback to a microcontroller so as to dynamically control the light source.

FIG. 9 is a block diagram of an exemplary system in which the light source is controlled by an electronic circuit with one or more sensors that operate in a closed loop to provide feedback to a microcontroller so as to dynamically control the light source during a treatment (irradiation) session. As can be seen, the electronic circuit is similar to that shown and described in connection with FIG. 8, with the addition of one or more sensors that operate in a closed loop to provide feedback to the microcontroller.

Certain sensors may be built into the layers of the device, while other sensors may be applied to the skin or other tissue surface of the subject. For example, optical sensors and/or electrical and acoustic impedance sensors may be used to monitor the color spectrum or image of a muscle contusion. Infrared imaging reflectance may also be used to evaluate the state of a muscle contusion and, in particular, the level of inflammation. As another example, electromyography (EMG) and ultrasonic imaging may be used to determine when a muscle has relaxed and recovered. It is also possible to use an external measurement of tissue hardness. In addition, performance can be measured with movement analysis using gyro sensors and accelerometers. Further, EMG sensors that detect muscle relaxation could be used to provide dose control, i.e., the light may be applied until there is a reduction in the EMG illustrative of decreased firing/relaxation of the muscle. Of course, other types of sensors may also be used in accordance with the invention.

IV. Studies: Reduction in Muscle Fatigue

Testing was performed to determine if the irradiation of a biceps muscle with pulsed blue and red light improves muscle function and/or decreases perceived exertion when applied after an elbow flexion fatigue protocol.

Study 1

Figure 10:
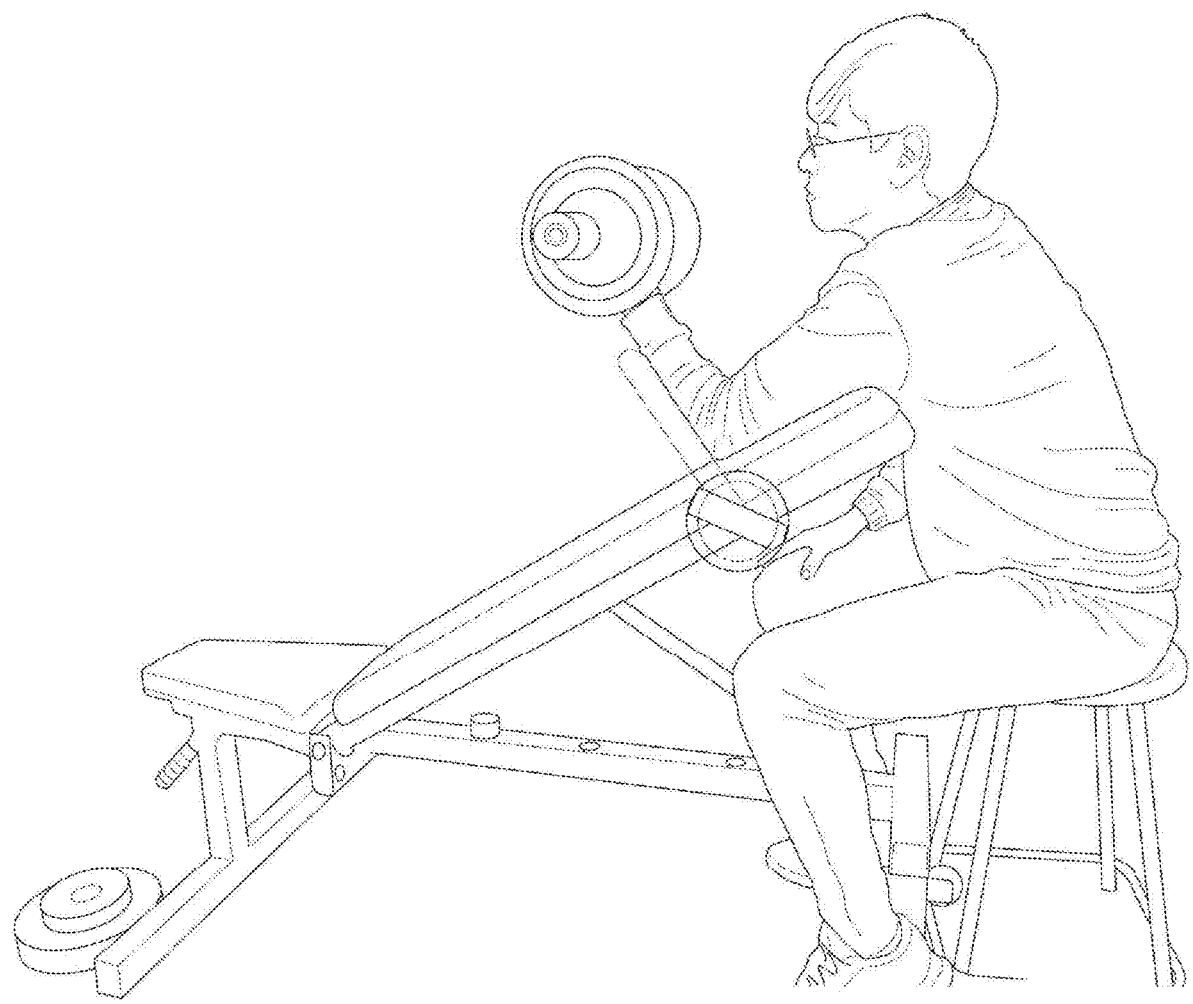
FIG. 10 is a side elevational view of a participant performing an elbow flexion fatigue task.
Figure 15:
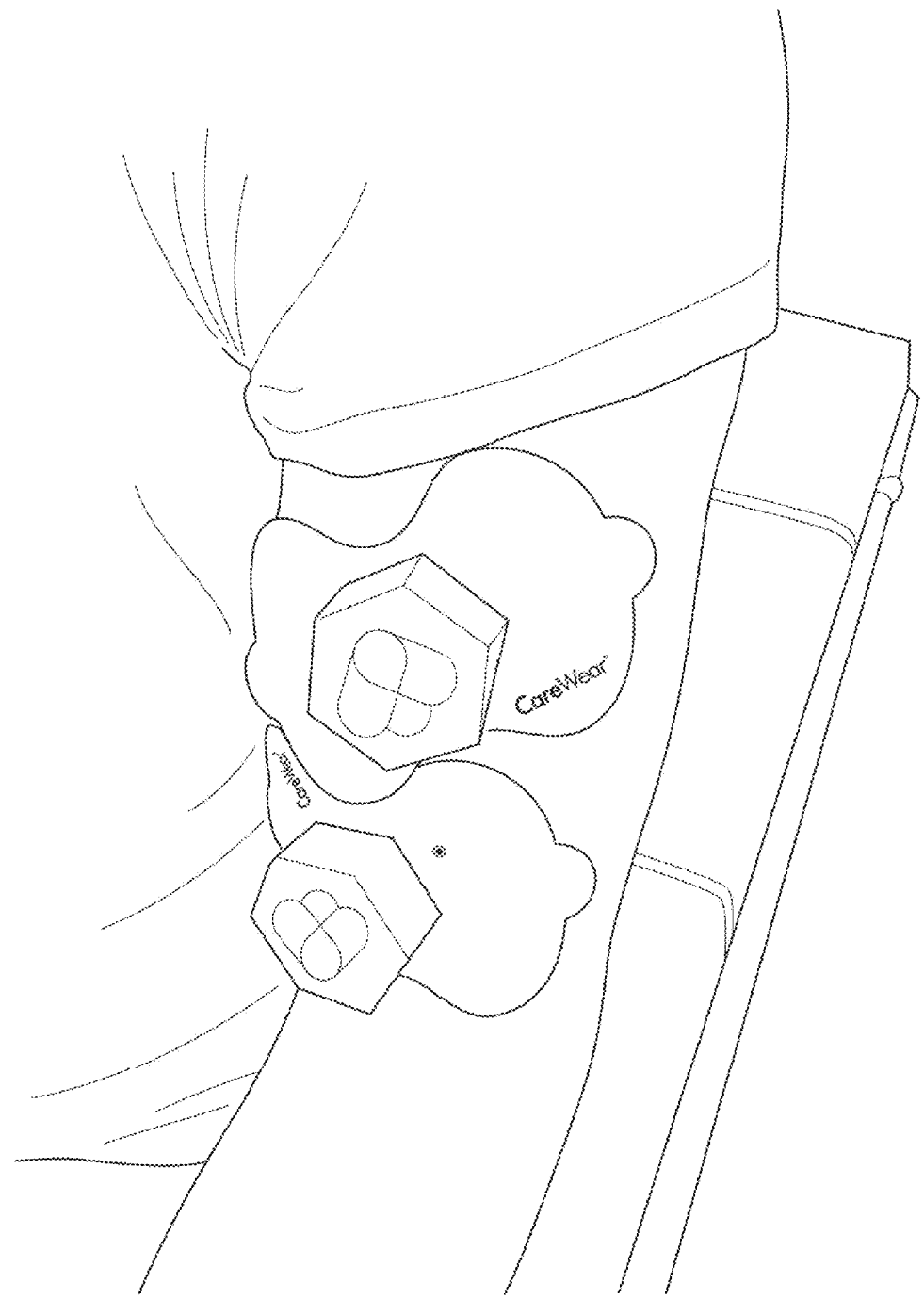
FIG. 15 is perspective view of a participant with two blue-red light patches positioned over the biceps brachii muscle during a light treatment.

In a first study, two groups of participants—an active group of fourteen participants and a sham group of fifteen participants—were tested in accordance with the following procedures:
1. Both groups of participants warmed up their biceps muscles with an exercise band.
2. Both groups of participants performed a first elbow flexion fatigue task. Specifically, with reference to FIG. 10, each participant was seated on a stool and his/her arm stabilized on an incline bench adjusted to 45°. The seated and arm position stabilized the participant from trying to use accessory muscles during the activity. A goniometer was taped onto the incline bench to mark 90° of elbow flexion. The participant was instructed to lower a dumbbell at a controlled speed to touch the incline bench, and perform a maximal elbow flexion exercise returning the dumbbell to the 90° starting point. Each participant performed as many repetitions as possible and was required to complete at least twenty-five repetitions per minute. If the participant rested or did not keep pace, the exercise was stopped.
3. Both groups of participants reported a post-exercise rated perceived exertion (RPE) score on the Borg scale (6 to 20 scale).
4. After the first elbow flexion fatigue task, a thirty-minute light treatment or sham treatment was administered based on the randomized group assignment. The light treatment for the participants in the active treatment group was applied using two light patches placed on the anterior brachium over the biceps brachii muscle, as shown in FIG. 15. The light patches each comprised the Firefly™ butterfly light patch available from Carewear Corp of Reno, Nev., which includes a printed LED film with 130 hexagon-shaped LED clusters laminated to a quantum dot film (as described above in connection with FIG. 3) and has an area of 50 cm². Each light patch delivered blue light at 450 nm and red light at 630 nm (75% blue light and 25% red light). The blue and red light was pulsed at a 33% duty cycle at a pulse repetition rate of 33 KHz with a peak irradiance of 9 mW/cm². The average irradiance was 3 mW/cm² and the radiant exposure (fluence) was 5 J/cm². The sham treatment for the participants in the sham treatment group was performed by turning on the power control for the light patches, but a switch built into the device allowed the investigator to turn off the power to the light patches. The participant was instructed that an infrared treatment was being applied, which wavelength is not in the visible spectrum and thus cannot be seen by the participant (when in fact no light treatment was applied to the participant).
5. Both groups of participants performed a second elbow flexion fatigue task, as described above.
6. Both groups of participants reported a post-exercise rated perceived exertion (RPE) score on the Borg scale (6 to 20 scale).

The data was then analyzed as a difference between the first elbow flexion fatigue task and the second elbow flexion fatigue task and the results were reported as follows.

Number of Repetitions

The Shapiro-Wilk test (P=0.041) indicated that the data was not normally distrusted so the Wilcoxon (Rank Sum) nonparametric test was used for the analysis. The results are shown in Table 1 below:

TABLE 1

| Level | Number | Mean | Std. Dev. | Std. Err. Mean | Lower 95% | Upper 95% |
| --- | --- | --- | --- | --- | --- | --- |
| Active | 14 | −3.3571 | 5.13820 | 1.3732 | −6.32 | −0.390 |
| Sham | 15 | −8.3333 | 6.89375 | 1.7800 | −12.15 | −4.516 |

Figure 11:
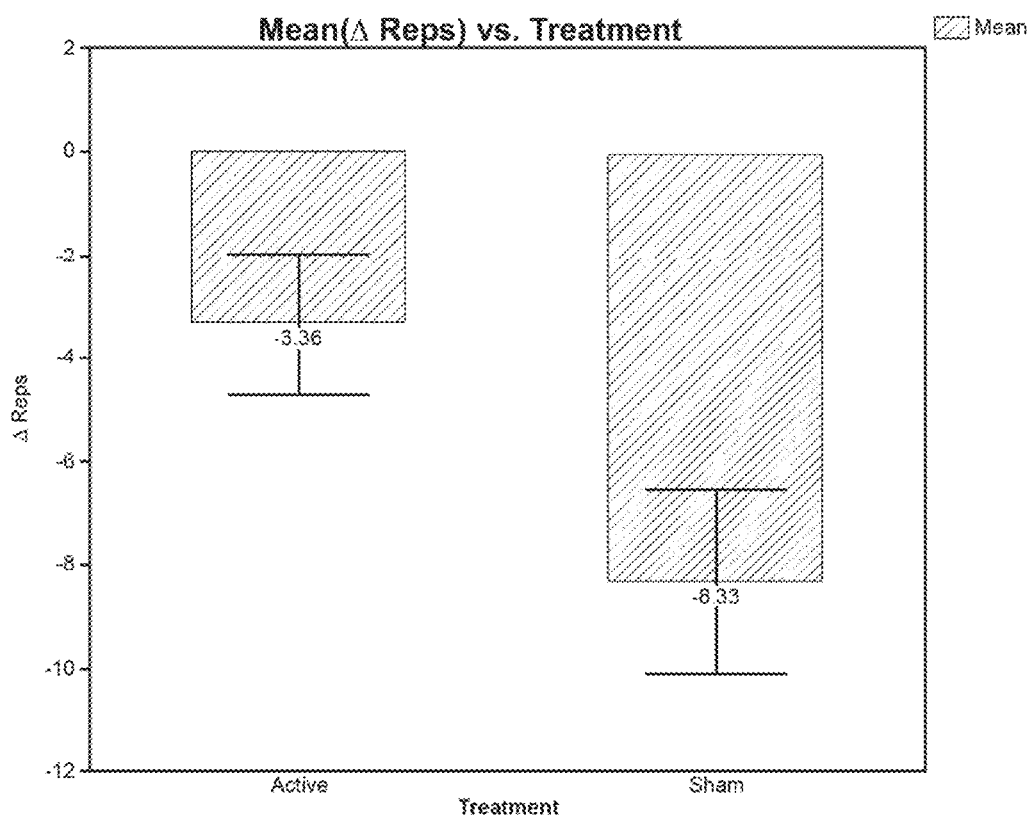
FIG. 11 is a graph depicting the mean change in repetitions between a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

As can be seen, there was a significant difference between the active and sham participant groups (chi square=3.872, P=0.491). The light treatment applied to the active participant group reduced the amount of muscle fatigue during the second elbow flexion fatigue task. FIG. 11 is a graph depicting the mean change in repetitions between the first elbow flexion fatigue task and the second elbow flexion fatigue task for each of the active group of participants and the sham group of participants, i.e. −3.33571 for the active participant group and −8.3333 for the sham participant group.

Borg RPE Score

The Shapiro-Wilk test (P=0.007) indicated that the data was not normally distrusted so the Wilcoxon (Rank Sum) nonparametric test was used for the analysis. The results are shown in Table 2 below:

TABLE 2

| Level | Number | Mean | Std. Dev. | Std. Err. Mean | Lower 95% | Upper 95% |
| --- | --- | --- | --- | --- | --- | --- |
| Active | 14 | 0.642857 | 1.33631 | 0.35714 | −0.1287 | 1.4144 |
| Sham | 15 | 0.266667 | 1.22280 | 0.31573 | −0.4105 | 0.9438 |

Figure 12:
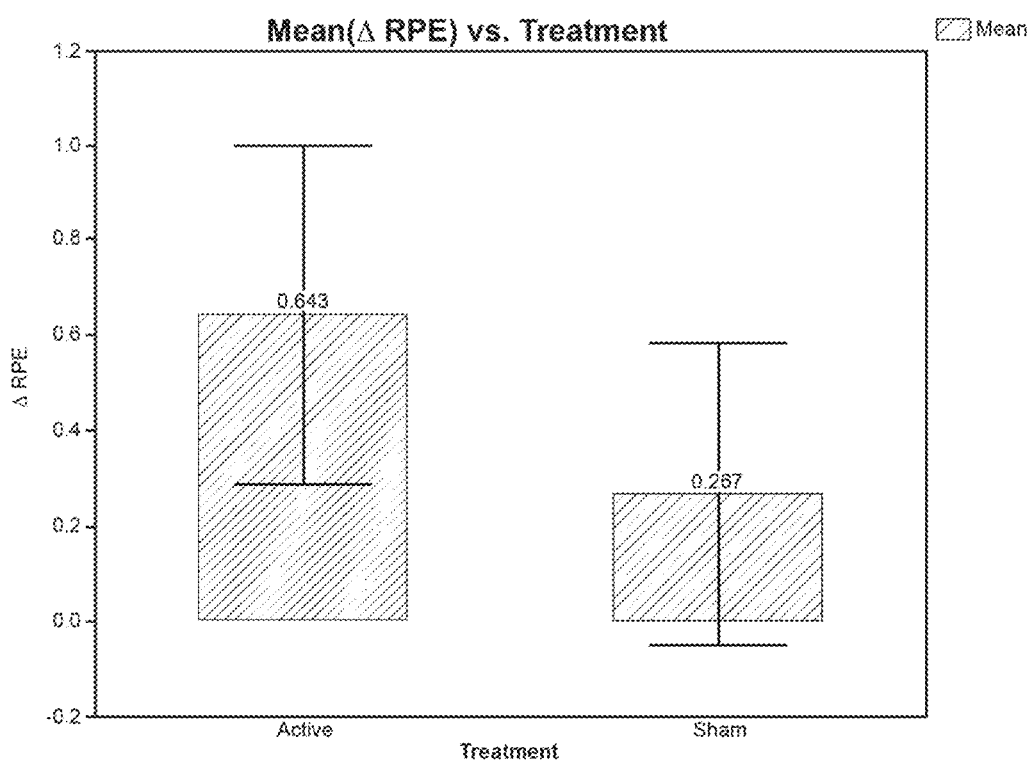
FIG. 12 is a graph depicting the mean change in rated perceived exertion (RPE) score between a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

As can be seen, there was no significant difference between the active and sham participant groups with respect to their ratings of perceived exertion (chi square=0.70, P=0.402). FIG. 12 is a graph depicting the mean change in RPE score between the first elbow flexion fatigue task and the second elbow flexion fatigue task for each of the active group of participants and the sham group of participants, i.e. 0.642857 for the active participant group and 0.266667 for the sham participant group.

Thus, at substantially the same perceived level of exertion, the participants who received a light treatment between the first and second elbow flexion fatigue tasks were able to perform a greater number of repetitions during the second elbow flexion fatigue task than the participants who did not receive any treatment.

Figure 13:
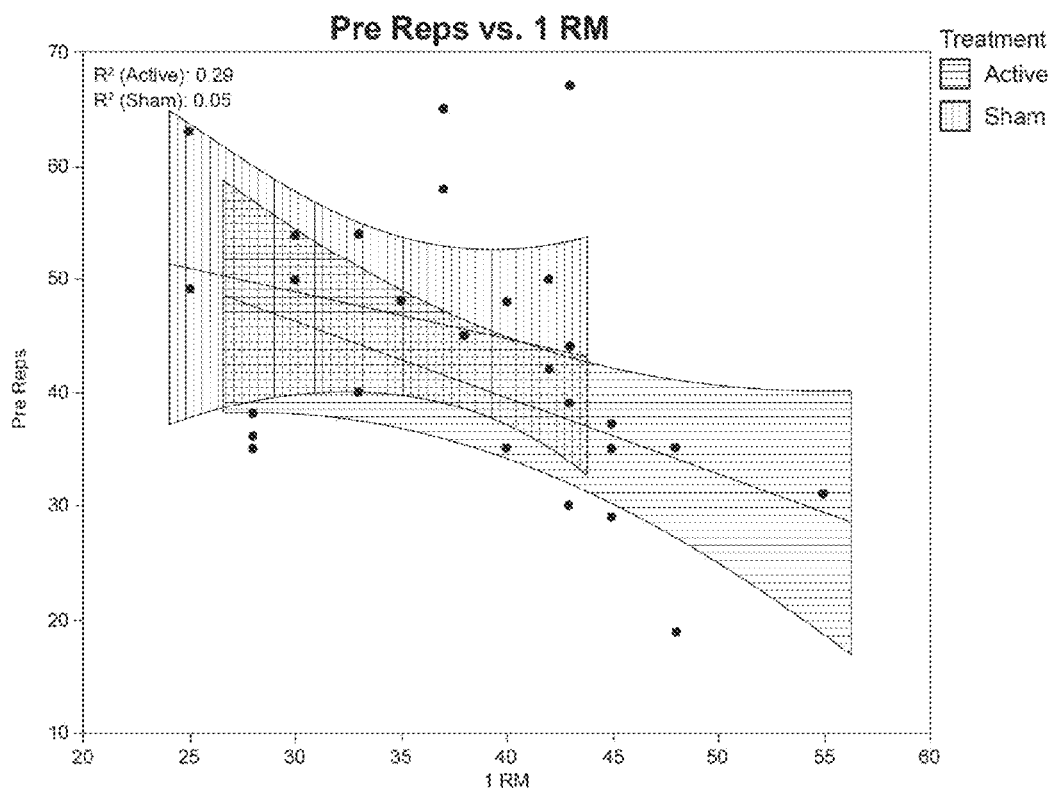
FIG. 13 is a graph depicting the maximum amount of weight that can be lifted during an elbow flexion fatigue task for one repetition (1 RM) in relation to the total number of repetitions during a first elbow flexion fatigue task for each of (a) an active group of participants who received a treatment of pulsed blue and red light between the first and second fatigue tasks and (b) a sham group of participants who did not receive any treatment between the first and second fatigue tasks.
Figure 14:
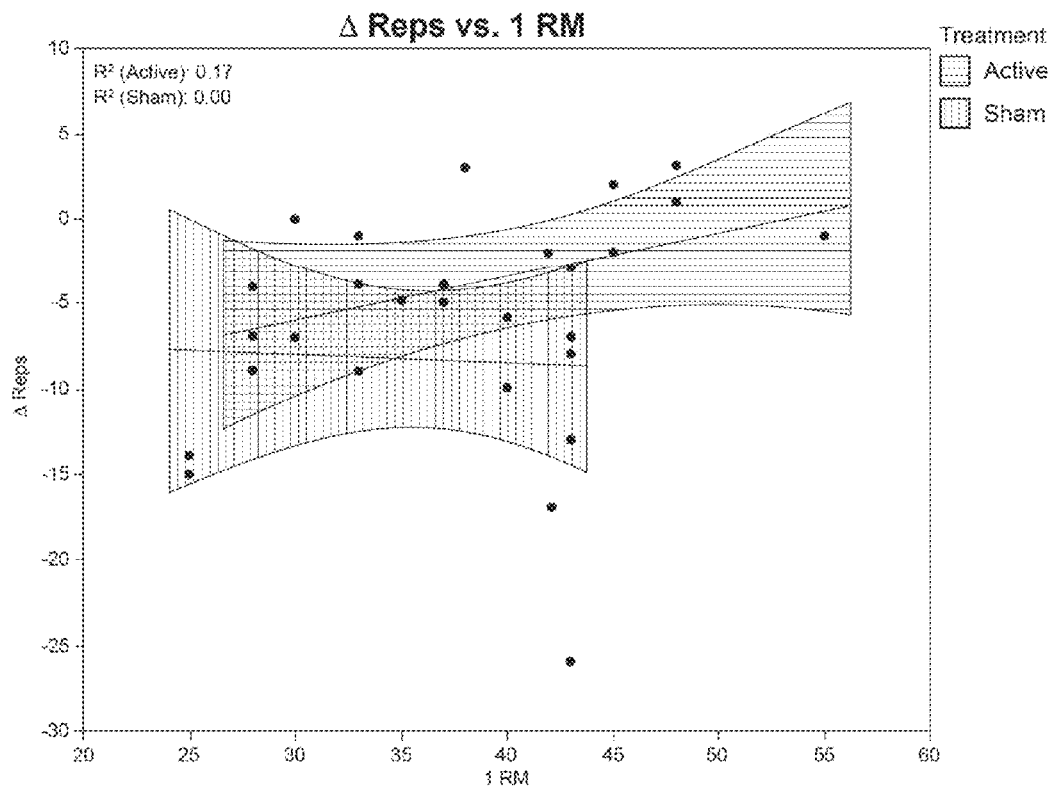
FIG. 14 is a graph depicting the maximum amount of weight that can be lifted during an elbow flexion fatigue task for one repetition (1 RM) in relation to the change in repetitions between a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

Finally, an additional analysis was performed to determine if there was a correlation between the maximum amount of weight that each participant could lift during an elbow flexion fatigue task for one repetition (1 RM) and (i) the total number of repetitions performed during the first elbow flexion fatigue task or (ii) the change in the number of repetitions between the first and second elbow flexion fatigue tasks. The data demonstrated that there was no such correlation. FIG. 13 is a graph depicting 1 RM in relation to the total number of repetitions during a first elbow flexion fatigue task for each of the active group of participants and the sham group of participants. FIG. 14 is a graph depicting 1 RM in relation to the change in repetitions between the first and second elbow flexion fatigue tasks for each of the active group of participants and the sham group of participants.

Study 2

In a second study, the participants consisted of thirty-two males and two females between the ages of 18 and 35 years (age=22.5±2.7 years). Prior to enrollment in the study, it was required that the participants perform upper extremity strength training at least two times per week for at least two months. It was also required that the participants be able to perform an elbow flexion exercise (i.e., biceps curl) with a 1 repetition maximum (RM) of at least twenty-five pounds. An individual was excluded from enrolling in the study if: (1) he/she had sustained a musculoskeletal injury to the shoulder or elbow area within the three months prior to enrollment; (2) he/she had used a nutritional supplement or pharmacological agent related to pain or muscle development within the two weeks prior to enrollment; or (3) he/she presented with contraindications or precaution related to photobiomodulation, such as cancer, recent organ transplant, epilepsy, had a steroid injection within the past three months, an acute infection, and/or suffered from a thyroid condition. The participants made two visits to the research laboratory.

First Visit

On the first visit, investigators recorded each participant's demographics (i.e., age, sex and ethnicity) and anthropometric measurements (i.e., height, mass, BMI and biceps girth). Each participant then warmed up his/her biceps muscles with an exercise band performing concentric movements of the shoulder and elbow. The movements included shoulder flexion, extension, abduction, internal rotation, and external rotation, as well as elbow flexion and extension. Each movement was completed for two sets and ten repetitions per set. After the warmup, the participants rested for five minutes.

Investigators then determined each participant's 1 RM during elbow flexion of his/her non-dominant arm. Specifically, with reference to FIG. 10, each participant was seated on a stool and his/her arm stabilized on an incline bench adjusted to 45°. The seated and arm position stabilized the participant from trying to use accessory muscles during the activity. A goniometer was taped onto the incline bench to mark 90° of elbow flexion. The participant was instructed to lower a dumbbell at a controlled speed to touch the incline bench, and perform a maximal elbow flexion exercise returning the dumbbell to the 90° starting point. The participant was allowed three attempts to find his/her 1 RM with his/her non-dominant arm. Increases or decreases of the weight were based on the participant's subjective perceived exertion of the previous repetition. After the 1 RM was determined, the participant rested for five minutes.

Each participant then performed an orientation of the elbow flexion fatigue task, with minimal weight, to limit potential task learning effects during the second visit (described below). Specifically, all weight was cleared from the dumbbell leaving a total weight of eight pounds. The muscle fatigue task was performed by starting with the weight at 90° elbow flexion. A metronome was set to fifty beats per minute. The participant was instructed to lower the weight to touch the bench on the first beat and raise the weight back to the 90° position on the second beat. The set speed created an exercise of twenty-five repetitions per minute. If the participant was not able to stay up with the pace or the participant was unable to perform the elbow flexion, the test was stopped.

Finally, the participants were randomly assigned to an active or sham treatment group by a random number draw so as to provide an active treatment group of seventeen participants and a sham treatment group of seventeen participants.

Second Visit

The participants returned to the research laboratory four days after the first visit. During the second visit, each participant performed the same warmup as that in the first visit, but added twenty repetitions of the elbow flexion fatigue task with no weight. After the warmup, the participant rested for five minutes.

Each participant then performed a first elbow flexion fatigue task using the same setup as that used for determining 1 RM during the first visit. The weight used for the fatigue task was set to 50% of the participant's 1 RM. The participant performed the fatigue task until he/she was not able to stay up with the pace or the participant was unable to perform the elbow flexion. The number of repetitions were counted by one of the investigators. Immediately after the fatigue task, the participant reported a post-exercise rated perceived exertion (RPE) score on the Borg scale (6 to 20 scale).

After the first elbow flexion fatigue task, a thirty-minute light treatment or sham treatment was administered based on the randomized group assignment.

The light treatment for the participants in the active treatment group was applied using two light patches placed on the anterior brachium over the biceps brachii muscle, as shown in FIG. 15. The light patches each comprised the Firefly™ butterfly light patch available from Carewear Corp of Reno, Nev., which includes a printed LED film with 130 hexagon-shaped LED clusters laminated to a quantum dot film (as described above in connection with FIG. 3) and has an area of 50 cm². Each light patch delivered blue light at 450 nm and red light at 645 nm (75% blue light and 25% red light). The blue and red light was pulsed at a 33% duty cycle at a pulse repetition rate of 33 KHz with a peak irradiance of 9 mW/cm², The average irradiance was 3 mW/cm² and the radiant exposure (fluence) was 5.4 J/cm².

The sham treatment for the participants in the sham treatment group was performed by turning on the power control for the light patches, but a switch built into the device allowed the investigator to turn off the power to the light patches. The participant was instructed that an infrared treatment was being applied, which wavelength is not in the visible spectrum and thus cannot be seen by the participant (when in fact no light treatment was applied to the participant).

Immediately after the light treatment, each participant performed a second elbow flexion fatigue task using the same setup as that used for the first fatigue task (i.e., the setup described above for determining 1 RM) and using the same weight as that used in the first fatigue task. The participant performed the fatigue task until he/she was not able to stay up with the pace or the participant was unable to perform the elbow flexion. The number of repetitions were counted by one of the investigators. Immediately after the fatigue task, the participant reported a post-exercise rated perceived exertion (RPE) score on the Borg scale (6 to 20 scale).

Data and Statistical Analysis

Figure 16:
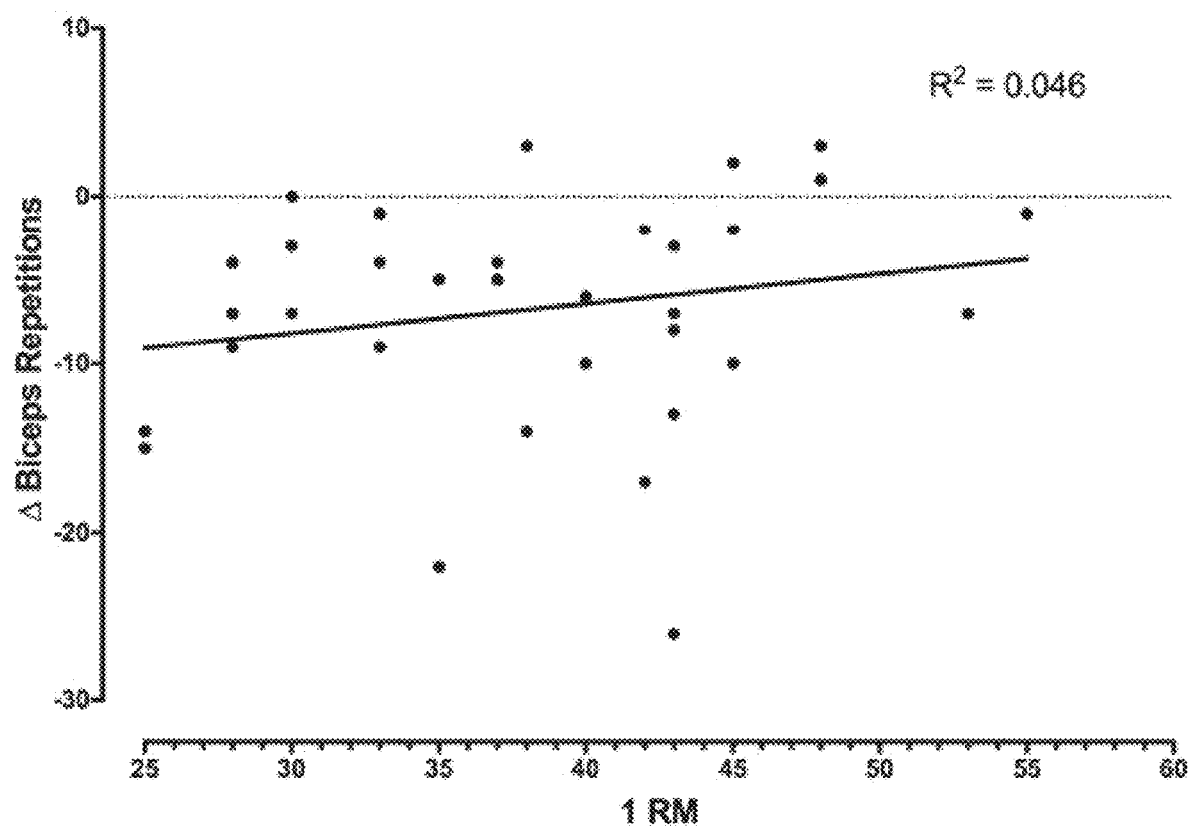
FIG. 16 is a graph depicting the maximum amount of weight that can be lifted during an elbow flexion fatigue task for one repetition (1 RM) in relation to the change in repetitions between a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

To determine demographic and pre-treatment differences, a t-test compared the demographic and pre-treatment fatigue task repetitions between the active and sham treatment groups. A linear regression was used to determine if there was a correlation between the maximum amount of weight that each participant could lift during an elbow flexion fatigue task for one repetition (1 RM) and the change in the number of repetitions between the first and second elbow flexion fatigue tasks. The data demonstrated that there was no such correlation (P=0.225). FIG. 16 is a graph depicting 1 RM in relation to the change in repetitions between the first and second elbow flexion fatigue tasks for each of the participants.

The data was normalized between the participants by using the change in pre-treatment to post-treatment fatigue task repetitions in an independent t-test to analyze the difference between treatment groups. Further, to determine the individual outcome of each participant, the data was coded as "positive" if a participant had a change count of ≥0 and "negative" if the change count was <0. A Fisher's exact test was used with this coded data to determine if there were differences between the treatment groups.

To determine if a participant perceived the intensity of exercise, using the Borg RPE scale, as being different between the pre-treatment and post-treatment fatigue tasks, a 2×2 (trial×treatment group) repeated measures ANOVA was used. All data analysis was completed using JMP Pro 13 (SAS, Inc., Cary, North Carolina) and with a set alpha level of P≤0.05.

Results

There were no significant demographic differences between the randomly assigned treatment groups. There was a significant difference in the participants' non-dominant elbow flexion 1 RM between the active (40.8±7.9 lbs) and sham (35.6±6.4 lbs) treatment groups ($t_{32}$=2.10, P=0.043). However, there was no correlation between the participants' 1 RM and change in fatigue task repetitions pre-treatment to post-treatment ($F_{1,33}$=1.534, P=0.225, $R^2$=0.046). The demographic and pre-treatment measurements are shown in Table 3 below:

TABLE 3

|  | Active | Sham | P-value |
| --- | --- | --- | --- |
| N | 17 | 17 |  |
| Age (years) | 22.4 ± 3.0 | 22.6 ± 2.5 | 0.807 |
| Sex (Female or Male) | F = 1, M = 16 | F = 1, M = 16 | 1.000 |
| Ethnicity (Hispanic or Non-Hispanic) | H = 6, Non-H = 11 | H = 9, Non-H = 8 | 0.491 |
| Height (cm) | 178.0 ± 9.4 | 174.6 ± 6.6 | 0.234 |
| Mass (kg) | 84.7 ± 14.5 | 78.8 ± 11.8 | 0.203 |
| BMI | 26.6 ± 3.8 | 25.9 ± 4.0 | 0.590 |
| Biceps Girth (cm) | 32.4 ± 3.3 | 31.0 ± 2.8 | 0.183 |
| 1 RM (lbs) | 40.8 ± 7.9 | 35.6 ± 6.4 | 0.043 (significant with alpha level set at P ≤ 0.05) |
| Pre-Treatment Reps | 40.8 ± 12.5 | 47.2 ± 11.5 | 0.133 |

Figure 17:
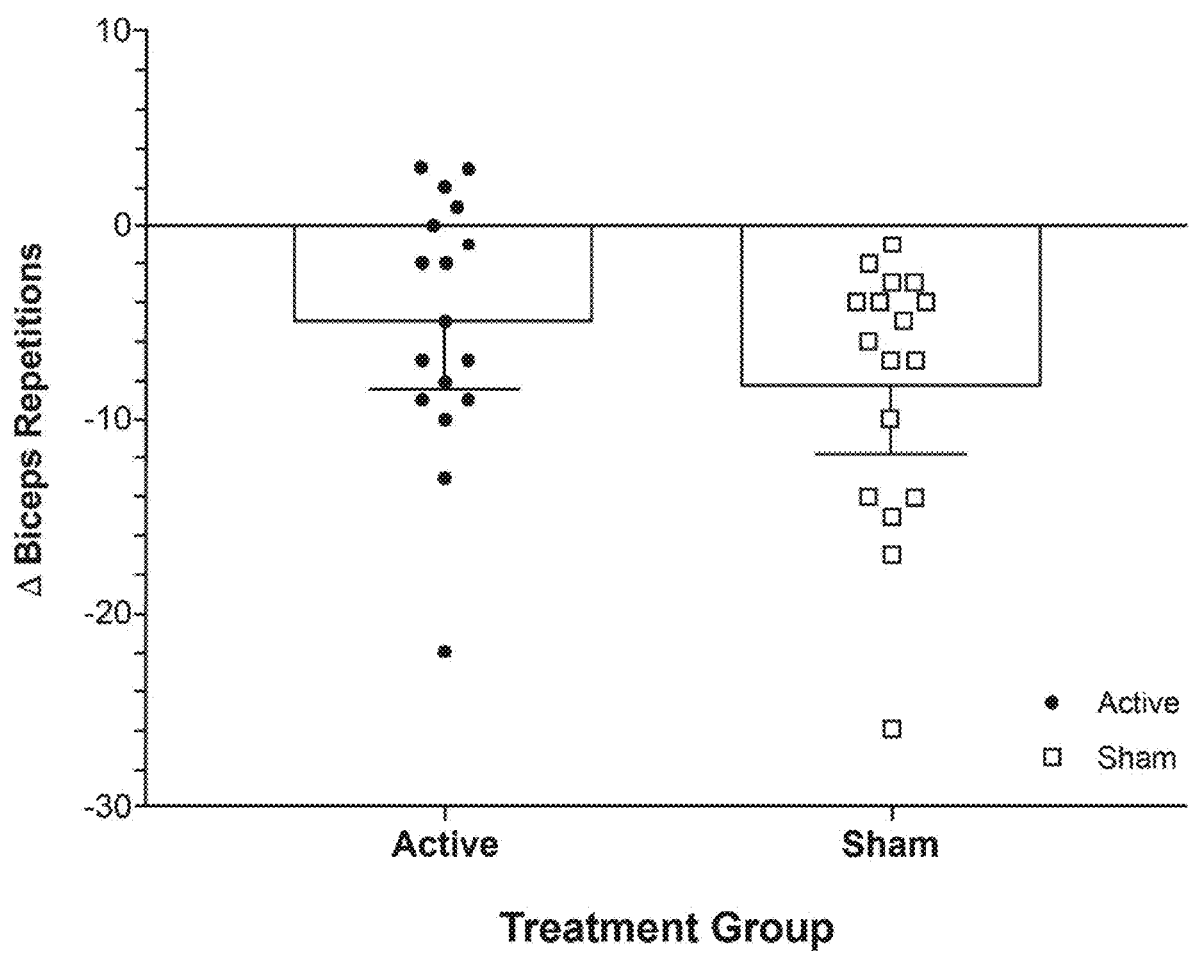
FIG. 17 is a graph depicting the mean and 95% confidence interval, with individual scatterplot, of the change in repetitions between a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

Overall, fatigue occurred between the two elbow flexion fatigue tasks (pre-treatment=44.1±12.3 and post-treatment=37.4±9.6 repetitions, $t_{66}$=2.511, P=0.015). The active treatment group had less muscle fatigue than the sham treatment group during the post-treatment fatigue task; however, this difference was not statistically significant ($t_{32}$=1.439, P=0.160). The change in pre-treatment to post-treatment fatigue task repetitions was −5.1±6.6 (95% confidence interval: −8.46 to −1.66) for the active treatment group and −8.3±6.7 (95% confidence interval: −11.82 to −4.89) for the sham treatment group. When analyzed for an individual positive outcome from pre-treatment to post-treatment, 29.4% of the participants in the active treatment group had the same or improved outcome during the post-treatment fatigue task compared to 0.0% of the participants in the sham treatment group (P=0.045). FIG. 17 is a graph depicting the mean and 95% confidence interval, with individual scatterplot, of the change in repetitions between the first fatigue task and the second fatigue task for each of the active treatment group and the sham treatment group.

Figure 18:
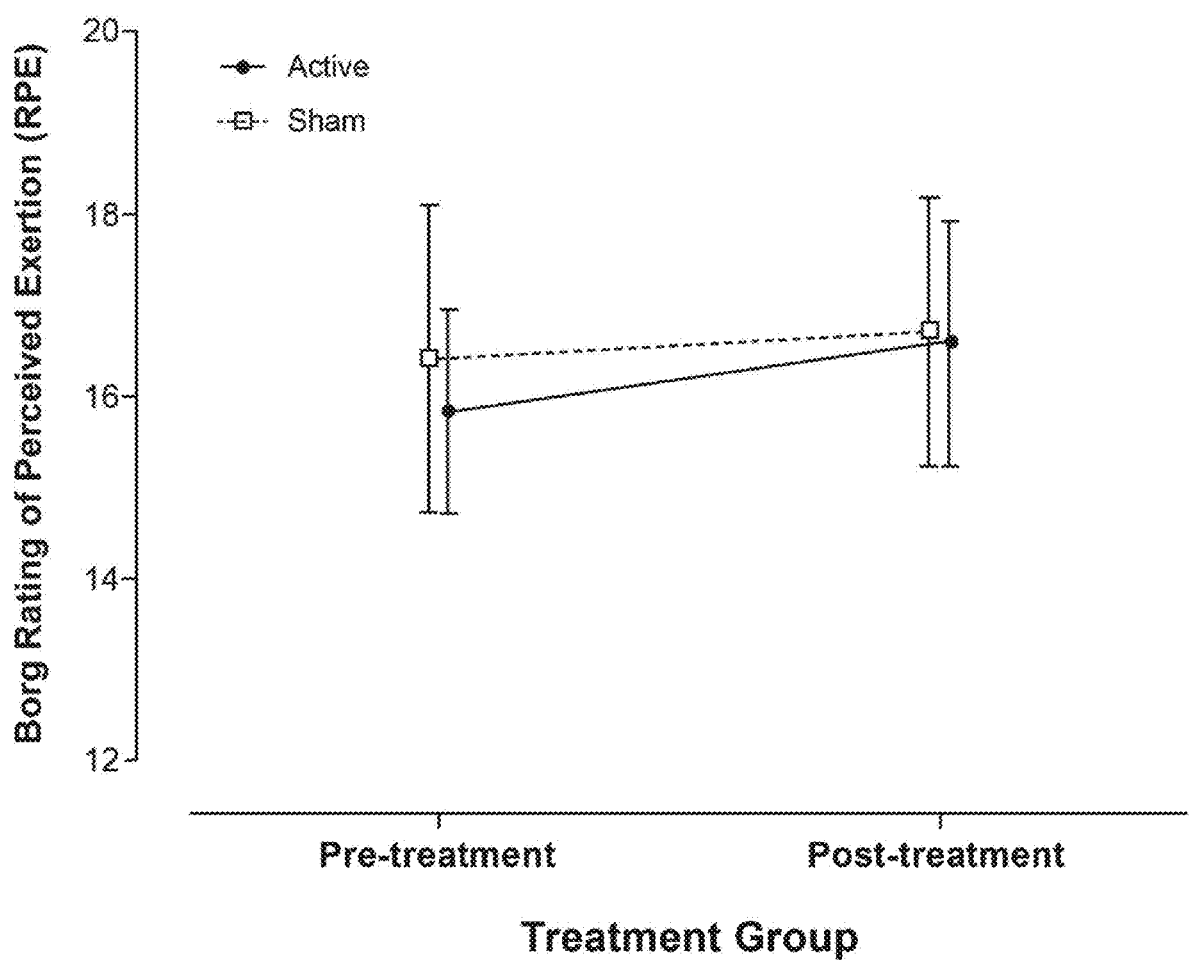
FIG. 18 is a graph depicting the mean and 95% confidence interval of the rated perceived exertion (RPE) score of a first elbow flexion fatigue task and a second elbow flexion fatigue task for each of (a) an active group of participants who received a treatment of pulsed blue and red light between the first and second fatigue tasks and (b) a sham group of participants who did not receive any treatment between the first and second fatigue tasks.

There was no significant difference between the participants ratings of perceived exertion (RPE) between the pre-treatment fatigue task and the post-treatment fatigue task (trial main effect) ($F_{1,67}$=0.622, P=0.433). There was also no significant difference between the active and sham treatment groups with respect to their ratings of perceived exertion (RPE) between the pre-treatment and post-treatment fatigue tasks (trial×treatment group interaction) ($F_{1,67}$=0.123, P=0.727). FIG. 18 is a graph depicting the mean and 95% confidence interval of the rated perceived exertion (RPE) score of a pre-treatment fatigue task and a post-treatment fatigue task for each of the active treatment group and the sham treatment group.

Thus, at substantially the same perceived level of exertion, 29.4% of the participants in the active treatment group had the same or improved result during the second fatigue task compared to the first fatigue task (i.e., after the light treatment), while no participants in the sham treatment group improved from the first fatigue task to the second fatigue task. It is believed that some individuals respond better to photobiomodulation therapy than others, as indicated by the resistance to muscle fatigue found in 29.4% of the participants in the active treatment group.

V. Study: Enhancement in Wound Healing

Further testing was performed to compare photobiomodulation and a placebo photobiomodulation on pain reduction and healing of quadriceps contusions.

Hypothesis

It was hypothesized that those treated with actual photobiomodulation for 30 minutes every day for five days at an average irradiance of 3 mW/cm$^2$ and a radiant exposure (fluence) of 5 J/cm$^2$, pulsed at a 33% duty cycle at a frequency of 33 KHz, using a combination of blue light at 450 nm and red light at 630 nm (75% blue light and 25% red light), produced using a printed LED film laminated to a quantum dot film (described above), would experience a greater decrease in pain and improved healing of quadriceps contusions than those treated with placebo photobiomodulation described to the subjects as an infrared lamp patch.

Subjects

Subjects were healthy males and females between the ages of 18-35. They did not have pain, were not diabetic, or pregnant, and had no injury to the lower extremity during the past two months.

Methods

Subject were screened to determine if they were qualified to be in the study. Subjects who met the criteria each had a photo taken of the area to be contused, and had imaging ultrasound applied to the proposed injury site to measure the qualities of the target tissue. Subjects then reported to tennis courts for the muscle contusion protocol. Using a tennis ball-serving machine, subjects were hit with a tennis ball in the belly of the quadriceps muscle. The tennis ball traveled at 136 kilometers/hour, for 26 cm until it struck the target tissue. Subjects then performed 10 squats and filled out a visual analog scale to mark their level of pain. Subjects then returned to the lab where a follow-up photo was taken, followed by imaging ultrasound. Each subject then received either an actual 30 minute photobiomodulation treatment or a placebo 30 minute photobiomodulation treatment. Immediately after the treatment, subjects performed 10 squats and filled out a visual analog scale to mark their level of pain, had a photo taken of the injury site, and received imaging ultrasound to determine the extent of the injury and the tissue compliance. Every day for four more days, subjects returned to the lab where they were treated with either an actual 30 minute photobiomodulation treatment or a placebo 30 minute photobiomodulation treatment. Pre and post measures of pain, ultrasound imaging and photography were obtained.

Results and Conclusion

Based on initial observations of 24 subjects, it was observed a more rapid decrease in pain, improved acceleration of healing based on the color transition of the bruise and a reduced muscle hardness on the subjects treated with the blue-red light patches as compared to the placebo.

VI. General

The description set forth above provides several exemplary embodiments of the inventive subject matter. Although each exemplary embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The use of any and all examples or exemplary language (e.g., "such as") provided with respect to certain embodiments is intended merely to better describe the invention and does not pose a limitation on the scope of the invention. No language in the description should be construed as indicating any non-claimed element essential to the practice of the invention.

The use of the terms "comprises," "comprising," or any other variation thereof, are intended to cover a non-exclusive inclusion, such that a method or device that comprises a list of elements does not include only those elements, but may include other elements not expressly listed or inherent to such method or device.

Unless defined otherwise, all technical and scientific terms used herein have the same meaning as commonly understood by one of ordinary skill in the art to which the disclosure pertains. Also, all ranges disclosed herein encompass any and all possible subranges. As will also be understood by one skilled in the art, a range includes each individual value within that range.

While the present invention has been described in detail above with reference to various exemplary embodiments, it should be understood that the invention is not limited to the specific methodologies or device configurations of these embodiments and that various modifications could be made to these embodiments without departing from the scope of the invention. In addition, although the exemplary embodiments are described as embodying several different inventive features, one skilled in the art will appreciate that any one of these features could be implemented without the others in accordance with the present invention.

What is claimed and desired to be secured by Letters Patent is as follows:

1. A method for reduction of muscle fatigue caused by strenuous activity or exercise, comprising: irradiating a muscle of a subject with pulsed blue light having a wavelength that ranges from 380 nm to 560 nm, wherein the pulsed blue light comprises a plurality of light pulses each of which has a pulse duration that ranges from 5 microseconds to 30 microseconds, wherein an off time between the light pulses ranges from 10 microseconds to 100 microseconds, and wherein the pulsed blue light has an average irradiance that ranges from 0.1 mW/cm$^2$ to 20 mW/cm$^2$ and is provided at a radiant exposure that ranges from 0.5 J/cm$^2$ to 60 J/cm$^2$ to thereby reduce muscle fatigue associated with the muscle.

2. The method of claim 1, wherein the pulsed blue light is applied over a belly of the muscle and a muscle innervation.

3. The method of claim 2, wherein the muscle comprises one of quadriceps, hamstrings, triceps surae, anterior tibias, abdominal muscles, erector spine muscles, core muscles, biceps, triceps, wrist extensors, shoulder musculature, upper, lower and mid back postural muscles, neck extensor/flexors, masseter and facial muscles, trapezius, elevator scapula, and intrinsic muscles of toes and fingers.

4. The method of claim 1, wherein the light pulses are provided at a pulse repetition rate that ranges from 33 kHz to 40 kHz.

5. The method of claim 1, wherein the pulsed blue light has an average irradiance that ranges from 1 mW/cm² to 5 mW/cm².

6. The method of claim 1, wherein the pulsed blue light is provided at a radiant exposure that ranges from 2.5 J/cm² to 30 J/cm².

7. The method of claim 1, wherein the pulsed blue light is provided at a radiant exposure that ranges from 3.6 J/cm² to 5 J/cm².

8. The method of claim 1, wherein the pulsed blue light is applied in accordance with an irradiation schedule that includes a plurality of irradiation sessions.

9. The method of claim 1, wherein the pulsed blue light is applied using a light source comprising one of printed light emitting diodes, organic light emitting diodes (OLEDs), phosphorescent OLEDs, lasers, light emitting diodes (LEDs), micro LEDs, polymer LEDs, quantum dot LEDs, and fluorescent tubes.

10. The method of claim 1, wherein the pulsed blue light is applied using a flexible light source configured to contact a surface to which it is applied.

11. The method of claim 10, wherein the flexible light source comprises a flexible light emitter positioned between a flexible anode and a flexible cathode.

12. The method of claim 11, wherein the flexible light emitter comprises one of (a) a plurality of blue light emitting diodes printed on a flexible film or (b) a plurality of organic light emitting diodes configured to emit blue light.

13. A method for enhancement of tissue repair, comprising: irradiating an injured tissue of a subject with pulsed blue light having a wavelength that ranges from 380 nm to 560 nm, wherein the pulsed blue light comprises a plurality of light pulses each of which has a pulse duration that ranges from 5 microseconds to 30 microseconds, wherein an off time between the light pulses ranges from 10 microseconds to 100 microseconds, and wherein the pulsed blue light has an average irradiance that ranges from 0.1 mW/cm² to 20 mW/cm² and is provided at a radiant exposure that ranges from 0.5 J/cm² to 60 J/cm² to thereby enhance healing of the injured tissue.

14. The method of claim 13, wherein the pulsed blue light is applied over an area where a muscle contusion has occurred.

15. The method of claim 13, wherein the pulsed blue light is applied over an area where a muscle, a ligament or a tendon has been stretched or torn.

16. The method of claim 13, wherein the pulsed blue light is applied over an open skin wound.

17. The method of claim 13, wherein the pulsed blue light is applied on a transparent wound dressing.

18. The method of claim 13, wherein the light pulses are provided at a pulse repetition rate that ranges from 33 kHz to 40 kHz.

19. The method of claim 13, wherein the pulsed blue light has an average irradiance that ranges from 1 mW/cm² to 5 mW/cm².

20. The method of claim 13, wherein the pulsed blue light is provided at a radiant exposure that ranges from 2.5 J/cm² to 30 J/cm².

21. The method of claim 13, wherein the pulsed blue light is provided at a radiant exposure that ranges from 3.6 J/cm² to 5 J/cm².

22. The method of claim 13, wherein the pulsed blue light comprises a plurality of light pulses provided at a duty factor that ranges from 20% to 33%.

23. The method of claim 13, wherein the pulsed blue light is applied in accordance with an irradiation schedule that includes a plurality of irradiation sessions.

24. The method of claim 13, wherein the pulsed blue light is applied using a light source comprising one of printed light emitting diodes, organic light emitting diodes (OLEDs), phosphorescent OLEDs, lasers, light emitting diodes (LEDs), micro LEDs, polymer LEDs, quantum dot LEDs, and fluorescent tubes.

25. The method of claim 13, wherein the pulsed blue light is applied using a flexible light source configured to contact a surface to which it is applied.

26. The method of claim 25, wherein the flexible light source comprises a flexible light emitter positioned between a flexible anode and a flexible cathode.

27. The method of claim 26, wherein the flexible light emitter comprises one of (a) a plurality of blue light emitting diodes printed on a flexible film or (b) a plurality of organic light emitting diodes configured to emit blue light.

28. A method for reduction of pain, comprising: irradiating an injured tissue of a subject with pulsed blue light having a wavelength that ranges from 380 nm to 560 nm, wherein the pulsed blue light comprises a plurality of light pulses each of which has a pulse duration that ranges from 5 microseconds to 30 microseconds, wherein an off time between the light pulses ranges from 10 microseconds to 100 microseconds, and wherein the pulsed blue light has an average irradiance that ranges from 0.1 mW/cm² to 20 mW/cm² and is provided at a radiant exposure that ranges from 0.5 J/cm² to 60 J/cm² to thereby provide a decrease in pain associated with the injured tissue.

29. The method of claim 28, wherein the pulsed blue light is applied over an area where a muscle contusion has occurred.

30. The method of claim 28, wherein the pulsed blue light is applied over an area where a muscle, a ligament or a tendon has been stretched or torn.

31. The method of claim 28, wherein the pulsed blue light is applied over an open skin wound.

32. The method of claim 28, wherein the pulsed blue light is applied on a transparent wound dressing.

33. The method of claim 28, wherein the light pulses are provided at a pulse repetition rate that ranges from 33 kHz to 40 kHz.

34. The method of claim 28, wherein the pulsed blue light has an average irradiance that ranges from 1 mW/cm² to 5 mW/cm².

35. The method of claim 28, wherein the pulsed blue light is provided at a radiant exposure that ranges from 2.5 J/cm² to 30 J/cm².

36. The method of claim 28, wherein the pulsed blue light is provided at a radiant exposure that ranges from 3.6 J/cm² to 5 J/cm².

37. The method of claim 28, wherein the pulsed blue light comprises a plurality of light pulses provided at a duty factor that ranges from 20% to 33%.

38. The method of claim 28, wherein the pulsed blue light is applied in accordance with an irradiation schedule that includes a plurality of irradiation sessions.

39. The method of claim 28, wherein the pulsed blue light is applied using a light source comprising one of printed light emitting diodes, organic light emitting diodes (OLEDs), phosphorescent OLEDs, lasers, light emitting diodes (LEDs), micro LEDs, polymer LEDs, quantum dot LEDs, and fluorescent tubes.

40. The method of claim 28, wherein the pulsed blue light is applied using a flexible light source configured to contact a surface to which it is applied.

41. The method of claim 40, wherein the flexible light source comprises a flexible light emitter positioned between a flexible anode and a flexible cathode.

42. The method of claim 41, wherein the flexible light emitter comprises one of (a) a plurality of blue light emitting diodes printed on a flexible film or (b) a plurality of organic light emitting diodes configured to emit blue light.

* * * * *